(12) United States Patent
Ivachtchenko et al.

(10) Patent No.: US 10,266,558 B2
(45) Date of Patent: Apr. 23, 2019

(54) MACROHETEROCYCLIC NUCLEOSIDE DERIVATIVES AND THEIR ANALOGUES, PRODUCTION AND USE THEREOF

(71) Applicants: Alexandre Vasilievich Ivachtchenko, Hallandale, FL (US); Andrey Alexandrovich Ivashchenko, Moscow (RU); Nikolay Filippovich Savchuk, Rancho Santa Fe, CA (US); ASAVI, LLC, Hallandale, FL (US); Alena Alexandrovna Ivachtchenko, Hallandale, FL (US); Oleg Dmitrievich Mitkin, Khimki (RU)

(72) Inventors: Alexandre Vasilievich Ivachtchenko, Hallandale, FL (US); Oleg Dmitrievich Mitkin, Khimki (RU); Andrey Alexandrovich Ivashchenko, Moscow (RU); Alena Alexandrovna Ivachtchenko, Hallandale, FL (US); Nikolay Filippovich Savchuk, Rancho Santa Fe, CA (US)

(*) Notice: Subject to any disclaimer, the term of this patent is extended or adjusted under 35 U.S.C. 154(b) by 0 days.

(21) Appl. No.: 15/287,805

(22) Filed: Oct. 7, 2016

(65) Prior Publication Data
US 2018/0099989 A1    Apr. 12, 2018

(51) Int. Cl.
*A61K 31/70*        (2006.01)
*A01N 43/04*        (2006.01)
(Continued)

(52) U.S. Cl.
CPC ........... *C07H 19/10* (2013.01); *A61K 31/708* (2013.01); *A61K 31/7068* (2013.01); *A61K 31/7072* (2013.01); *A61K 31/7076* (2013.01); *A61K 45/06* (2013.01); *A61K 31/706* (2013.01); *A61K 31/7052* (2013.01); *A61K 31/7056* (2013.01); *A61K 31/7064* (2013.01); *A61K 31/7084* (2013.01)

(58) Field of Classification Search
None
See application file for complete search history.

(56) References Cited

U.S. PATENT DOCUMENTS 8,889,701 B1 * 11/2014 Ivachtchenko ..... C07F 9/65586
514/274

OTHER PUBLICATIONS

Stahly Crystal Growth & Design (2007), vol. 7, pp. 1007-1026.*
Newman et al. "Solid-state analysis of the active pharmaceutical ingredient in drug products", DDT (2003), vol. 8, pp. 898-905.*

* cited by examiner

Primary Examiner — Patrick T Lewis

(57) ABSTRACT

Nucleosides and nucleotides (nucleos(t)ides) have been in clinical use for almost 50 years and have become cornerstones of treatment for patients with viral infections or cancer. The approval of several additional drugs over the past decade demonstrates that this family still possesses strong potential. Therefore nucleos(t)ide are of great interest as promising chemotherapeutic agents, including: 2'-deoxy-L-uridine (CAS № 31501-19-6), 2'-deoxy-D-uridine (CAS № 951-78-0), telbivudine (CAS № 3424-98-4), zidovudine (AZT, CAS № 30516-87-1), trifluridine (CAS № 70-00-8), clevudine (CAS № 163252-36-6), PSI-6206 (CAS № 863329-66-2), 2'-(S)-2'-chloro-2'-deoxy-2'-fluorouridine (CAS № 1673560-41-2), ND06954 (CAS № 114248-23-6), stavudine (CAS № 3056-17-5), 5-ethynyltavudine (Festinavir, CAS № 634907-30-5), torcitabine (CAS № 40093-94-5), (−)-beta-D-(2R,4R)-dioxolane-thymine (DOT, 1-((2R,4R)-2-(hydroxymethyl)-1,3-dioxolan-4-yl)-5-methyl-2,4(1H,3H)-pyrimidinedione, CAS No. 127658-07-5), 2-(6-amino-purin-9-yl)-ethanol (CAS № 707-99-3), 2'-C-methylcytidine (CAS № 20724-73-6), PSI-6130 (CAS № 817204-33-4), gemcitabine (CAS № 95058-81-4), 2'-chloro-2'-deoxy-2'-fluorocytidine (CAS № 1786426-19-4), 2',2'-dichloro-2'-deoxycytidine (CAS № 1703785-65-2), 2'-C-methylcytidine (CAS № 20724-73-6), PSI-6130 (CAS № 817204-33-4), lamivudine (3TC, CAS № 134678-17-4), emtricitabine (CAS № 143491-57-0), 2'-deoxyadenosine (CAS № 958-09-8), 2'-deoxy-β-L-adenosine (CAS № 14365-45-8), 2'-deoxy-4'-C-ethynyl-2-fluoroadenosine (CAS № 865363-93-5), didanosine (CAS № 69655-05-6), entecavir (CAS № 209216-23-9), FMCA (CAS № 1307273-70-6), dioxolane-G (DOG, CAS № 145514-01-8), β-D-2'-deoxy-2'-(R)-fluoro-2'-β-C-methylguanosine (CAS No 817204-45-8), abacavir (ABC, CAS № 136470-78-5), dioxolane-A (DOA, CAS #145514-02-9), [(2R,4R)-4-(6-cyclopropylamino-purin-9-yl)-[1,3]dioxolan-2-yl]-methanol (CAS № 1446751-04-7), amdoxovir (AMDX, CAS № 145514-04-1), (R)-1-(6-amino-purin-9-yl)-propan-2-ol (CAS № 14047-28-0), and [(2S,5R)-5-(6-amino-purin-9-yl)-4-fluoro-2,5-dihydro-furan-2-yl]-methanol.

Macroheterocyclic nucleoside derivative and its analog of the general formula 1 or general formula 2, a stereoisomer, isotope-enriched analog, pharmaceutically acceptable salt, hydrate, solvate, or crystalline or polymorphic form thereof,

1

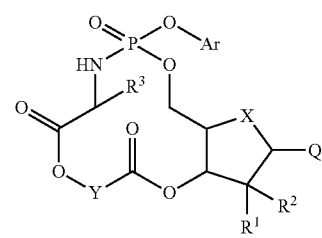

(Continued)

-continued

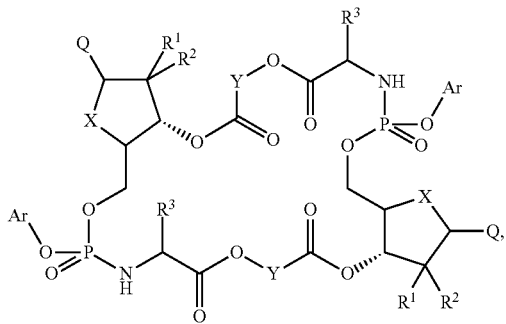

2

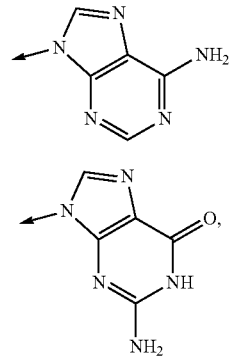

Q3

Q4 wherein:
Ar is aryl or hetaryl;
$R^1$ and $R^2$ are not necessarily the same substituents selected from H, F, Cl, $CH_3$, OH;
$R^3$ is H or $CH_3$;
X is oxygen or ethanediyl-1,1 ($C=CH_2$);
Y is $CH(R^4)(CH_2)_k$, $CH(R^4)(CH_2)_mC(O)O(CH_2)_n$;
$R^4$ is H or $CH_3$;
k has a value from zero to six;
m has a value from zero to two;
n has a value of one to four;
Q is a radical selected from Q1-Q4;

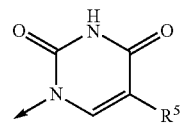

Q1

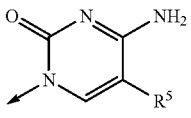

Q2 wherein: $R^5$ is the substituent selected from H, F, Cl, $CH_3$, OH;

the arrow (→) indicates the location, joined by Q1-Q4.

4 Claims, No Drawings

(51) Int. Cl.
| | | |
|---|---|---|
| *C07H 19/10* | (2006.01) |
| *A61K 31/7072* | (2006.01) |
| *A61K 45/06* | (2006.01) |
| *A61K 31/7068* | (2006.01) |
| *A61K 31/7076* | (2006.01) |
| *A61K 31/708* | (2006.01) |
| *A61K 31/7064* | (2006.01) |
| *A61K 31/7056* | (2006.01) |
| *A61K 31/706* | (2006.01) |
| *A61K 31/7084* | (2006.01) |
| *A61K 31/7052* | (2006.01) |

MACROHETEROCYCLIC NUCLEOSIDE DERIVATIVES AND THEIR ANALOGUES, PRODUCTION AND USE THEREOF

FIELD OF INVENTION

The present invention relates to macroheterocyclic nucleoside derivatives and their analogues, production and use thereof. These compounds are the prodrugs for treating viral and cancerous diseases and are inhibitors of HCV NSSB polymerase, HBV DNA polimerase and HIV-1 reverse transcriptase (RT).

BACKGROUND

Nucleosides and nucleotides (nucleos(t)ides) have been in clinical use for almost 50 years and have become cornerstones of treatment for patients with viral infections or cancer. The approval of several additional drugs over the past decade demonstrates that this family still possesses strong potential. Therefore nucleos(t)ide are of great interest as promising chemotherapeutic agents, including: 2'-deoxy-1-uridine (CAS № 31501-19-6), 2'-deoxy-D-uridine (CAS № 951-78-0), telbivudine (CAS № 3424-98-4), zidovudine (AZT, CAS № 30516-87-1), trifluridine (CAS № 70-00-8), clevudine (CAS № 163252-36-6), PSI-6206 (CAS № 863329-66-2), 2'-(S)-2'-chloro-2'-deoxy-2'-fluorouridine (CAS № 1673560-41-2), ND06954 (CAS № 114248-23-6), stavudine (CAS № 3056-17-5), 5-ethynyltavudine (Festinavir, CAS № 634907-30-5), torcitabine (CAS № 40093-94-5), (−)-beta-D-(2R,4R)-dioxolane-thymine (DOT, 1-((2R,4R)-2-(hydroxymethyl)-1,3-dioxolan-4-yl)-5-methyl-2,4 (1H,3H)-pyrimidinedione, CAS № 127658-07-5), 2-(6-amino-purin-9-yl)-ethanol (CAS № 707-99-3), 2'-C-methylcytidine (CAS № 20724-73-6), PSI-6130 (CAS № 817204-33-4), gemcitabine (CAS № 95058-81-4), 2'-chloro-2'-deoxy-2'-fluorocytidine (CAS № 1786426-19-4), 2',2'-dichloro-2'-deoxycytidine (CAS № 1703785-65-2), 2'-C-methylcytidine (CAS № 20724-73-6), PSI-6130 (CAS № 817204-33-4), lamivudine (3TC, CAS № 134678-17-4), emtricitabine (CAS № 143491-57-0), 2'-deoxyadenosine (CAS № 958-09-8), 2'-deoxy-β-L-adenosine (CAS № 14365-45-8), 2'-deoxy-4'-C-ethynyl-2-fluoroadenosine (CAS № 865363-93-5), didanosine (CAS № 69655-05-6), entecavir (CAS № 209216-23-9), FMCA (CAS № 1307273-70-6), dioxolane-G (DOG, CAS № 145514-01-8), β-D-2'-deoxy-2'-(R)-fluoro-2'-β-C-methylguanosine (CAS № 817204-45-8), abacavir (ABC, CAS № 136470-78-5), dioxolane-A (DOA, CAS #145514-02-9), [(2R,4R)-4-(6-cyclopropylamino-purin-9-yl)-[1,3]dioxolan-2-yl]-methanol (CAS № 1446751-04-7), amdoxovir (AMDX, CAS № 145514-04-1), (R)-1-(6-amino-purin-9-yl)-propan-2-ol (CAS № 14047-28-0), and [(2S,5R)-5-(6-amino-purin-9-yl)-4-fluoro-2,5-dihydro-furan-2-yl]-methanol [M. J. Sofia. Nucleosides and Nucleotides for the treatment of viral diseases. In *Annual Reports in Medicinal Chemistry* 2014, Volume 49, Editor-in-Chief M. C. Desai, p 221-247. L. P. Jordheim et al. Advances in the development of nucleoside and nucleotide analogues for cancer and viral diseases. *Nat. Rev. Drug. Discov.* 2013, 12(6), 447-464.].

Currently, nucleos(t)ides are the preferred option and standard of care for treating patients infected with hepatitis B virus (HBV) and they are emerging as a key component in therapies to treat hepatitis C virus (HCV) infection. They also play a central role in the management of other viral infections such as those caused by herpes viruses (HSV-1 and HSV-2), varicella zoster virus, Epstein-Barr virus, and cytomegalovirus [E. De Clercg. Ed. *Antiviral Agents* 2013, Vol. 67: Academic Press: New York. 2013. L. P. Jordheim et al. Advances in the development of nucleoside and nucleotide analogues for cancer and viral diseases. *Nal. Rev.* 2013,12, 447-464.]. The attractiveness of a nucleos(t)ide strategy in the development of therapeutics for vital diseases sterns from the fact that all viruses require a polymerase for either DNA or RNA replication.

Another factor that must be considered when developing a nucleos(t)ide inhibitor pertains to nucleos(t)ide metabolic activation. It is the nucleotide triphosphate analog, as the functional substrate for the viral polymerase that becomes incorporated into the growing RNA or DNA chain, typically leading to a chain termination event and ultimately an end to viral replication. Consequently, the efficiency by which a nucleos(t)ide gets converted to the active triphosphate and the concentration and half-life of the triphosphate within the cell are important factors in how effective the nucleos(t)ide is as an inhibitor of viral replication. In general, the first phosphorylation step is the most discriminating among the three needed to generate the active triphosphate. In cases where the nucleoside itself is not a good substrate for the kinase involved in the initial phosphorylation step, delivery of the monophosphate is desired, but this typically requires the use of prodrug technology to mask the unfavorable characteristics of the phosphate group and facilitate permeability. Consequently, nucleotide prodrug strategies have seen much use in the development of nucleotides to treat viral and cancer diseases.

Recently, the uridine nucleotide prodrug Sovaldi® (sofosbuvir, PSI-7977; GS-7977) [M. J. Sofia et al. Discovery of a β-D-20-Deoxy-20-r-fluoro-20-β-C-methyluridine Nucleotide Prodrug (PSI-7977) for the Treatment of Hepatitis C Virus. *J Med. Chem.* 2010, 53, 7202-7218. M. J. Sofia et al. Nucleoside phosphoramidate prodrugs. U.S. Pat. No. 7,964,580 (2011).] became the first nucleos(t)ide approved by both the FDA and EU regulatory authorities for the treatment of HCV patients infected with genotype (gT) 1, 2, 3, and 4 HCV virus and in clinical trials it also showed efficacy against all relevant HCV gTs (1-6) [I. M. Jacobson et al. Sofosbuvir for hepatitis C genotype 2 or 3 in patients without treatment options. *Engl. J. Med.* 2013, 368, 1867-1877. E. Lewirz et al. Sofosbuvir for previously untreated chronic hepatitis C infection. *Engl. J. Med.* 2013, 368, 1878-1887]. Its approval marked the first introduction of an all-oral interferon (IFN)-free regimen to treat patients suffering from HCV infection.

Also other known chemotherapeutic agents include phosphoramidate moieties to treat hepatitis C, including AVI-4201 [A. V. Ivachtchenko et al. Alkyl 2-{[(2r, 3s, 5r)-5-(4-amino-2-oxo-2H-pyrimidin-1-yl)-3-hydroxy-tetrahydro-furan-2-yl-methoxy]-phenoxy-phosphoryl-amino}-propionates, nucleoside inhibitors of HCV NSSB RNA-polymerase, and methods for producing and use thereof. WO2014148949, 2014], AVI-4203 [A. V. Ivachtchenko et al. Substituted (S)-(2R, 3R, 5R)-3-hydroxy-(5-pyrimidin-1-yl)-tetrahydrofuran-2-ylmethyl aryl phosphoramidate. U.S. Pat. No. 8,889,701, 2014] or CC-1845 [D. L Mayers. Development of Potent Novel Oral Pan-genotypic HCV Nucleotide, NS5A, NS5B non-nucleoside, and Helicase Inhibitors. 2015. https://www.informedhorizons.com/hepdart2015/pdf/Presentations/Mayers.pdf].

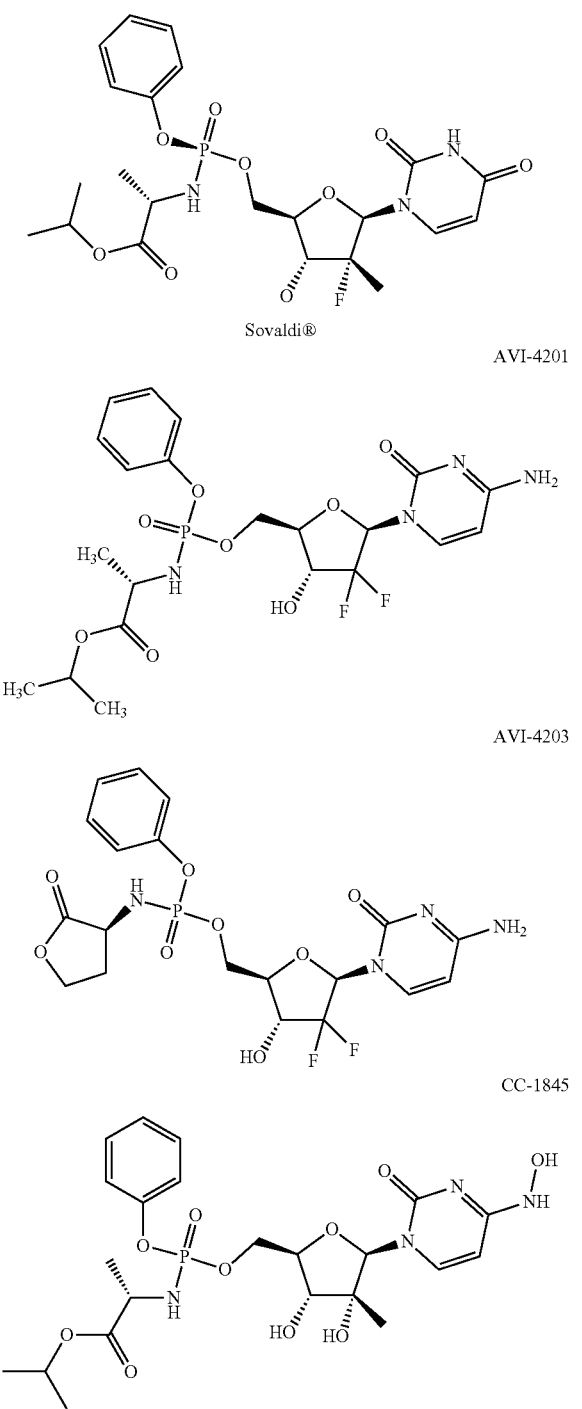

Should be noted that in this case the inhibitory activity of HCV NS5B RNA-polymerase phosphoramidate inhibitors Sovaldi®, AVI-4201 AVI-4203 ħ CC-1845 by orders of magnitude higher than that of the corresponding nucleoside: PSI-6206, Gemcitabine and 2'-C-Methylcytidine.

Other guanosine nucleotide prodrugs have been investigated, also employing the phosphoramidate prodrug moiety in an attempt to leverage liver targeting. Thus, PSI-353661 demonstrated potent inhibition in the replicon assay ($EC_{90}$=0.008 μM→1000-fold increase in potency compared to the guanosine analogue-β-D-2'-deoxy-2'-R-fluoro-2'-β-C-methylguanosine (Table 1).) and a novel resistance profile similar to PSI-352938, but was never progressed into clinical development [W. Clung et al. Discovery of PSI-353661, a Novel Purine Nucleotide. *ACS Med. Chem. Lett.* 2011. 2. 130-135.]. The structurally related pro-drugs IDX-184 ($EC_{50}$=0.4 μM) [X.-J. Zhou. Et al. Safety and Pharmacokinetics of IDX184, a Liver-Targeted Nucleotide Polymerase Inhibitor of Hepatitis C Virus, in Healthy Subjects. *Antimicrob. Agents Chemother.* 2011, 55, 76-81. J. Lalezari, et al. Short-Term Monotherapy with IDX184, a Liver-Targeted Nucleotide Polymerase Inhibitor, in Patients with Chronic Hepatitis C Virus Infection. *Antimicrob. Agents Chemother.* 2012. 56, 6372-6378.] and INX-08189 (BMS-986094, $EC_{50}$=0.010 μM) [C. McGuigan et al. Phosphorodiamidates as a Promising New Phosphate Prodrug Motif for Antiviral Drug Discovery: Application to Anti-HCV Agents. *J. Med. Chem.* 2011, 54, 8632-8645. J. H. Vernachio et al. MX-08189, a phosphoramidate prodrug of 6-O-methyl-2'-C-methyl guanosine, is a potent inhibitor of hepatitis C virus replication with excellent pharmacokinetic and pharmacodynamic properties. *Antimicrob. Agents Chemother.* 2011. 55, 1843-1851.], each producing an identical triphosphate, were progressed into the clinic, but severe cardiovascular toxicity associated with INX-08189 resulted in discontinuation of development for both compounds [J. J. Arnold et al. Sensitivity of Mitochondrial Transcription and Resistance of RNA Polymerase II Dependent Nuclear Transcription to Antiviral Ribonucleosides. *PLOS Pathog.* 2012. 8, DOI: 10.1371/journal.ppat. 1003030.]. The severe nature of the cardiovascular toxicity seen with INX-08189 seems to have curtailed the interest in developing a guanosine nucleoside for treating HCV patients.

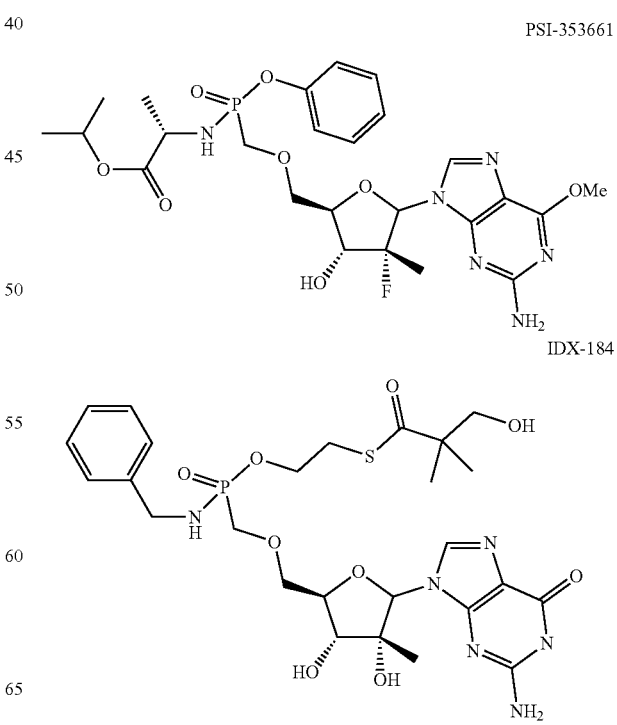

-continued

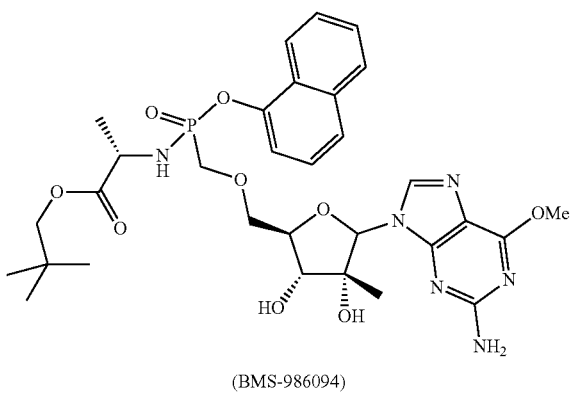

(BMS-986094)

HBV is a DNA virus in the Hepadnaviridae family. It is estimated that 400 million individuals are infected with HBV worldwide. The current standard of care for treatment of HBV is long-term nucleos(t)ide therapy. The nucleos(t)ides approved for treating HBV infection include lamivudine, adefovir dipivoxil, entecavir, telbivudine, and TDF. Entecavir and TDF are the most widely prescribed of these agents. Long-term use of entecavir leads to resistance in a significant patient population and TDF is associated with nephrotoxicity and bone loss [D. Grimm et al. HBV life cycle and novel drug targets. *Hepatol. Int.* 2011. 5. 644-653. G. Borgia, I. Gentile. Treating chronic hepatitis B: today and tomorrow. *Curr. Med. Chem.* 2006. 13. 2839-2855.]. However, continued use of nucleos(t)ide therapy has been associated with reduction in liver fibrosis demonstrating that suppression of viral replication has positive long-term value [T. T. Chang et al. Long-term entecavir therapy results in the reversal of fibrosis/cirrhosis and continued histological improvement in patients with chronic hepatitis B. *Hepatology* 2010. 52, 886-893. P. Marcellin et al. Regression of cirrhosis during treatment with tenofovir disoproxil fumarate for chronic hepatitis B: a 5-year open-label follow-up study. *Lancet* 2013, 381, 468-475.].

Even with the success of existing nucleos(t)ide HBV therapy, work has continued in an effort to identify, novel inhibitors that may provide additional benefit relative to the existing agents, and several of the anti-HW agents mentioned above have also been assessed for us in treating HBV infection [C. A. Geng et al. Small-molecule inhibitors for the treatment of hepatitis B virus documented in patents. *Mini Rev. Med. Chem.* 2013. 13, 749-776.].

Recently, preparation of the 2'-fluoro-6'-methylene-carbocyclic adenosine (FMCA) ($EC_{50}=0.55$ µM), which borrowed the 6'-methylene-carbocyclic nucleus of entecavir, led to a potent inhibitor of HBV replication that was also active against the lamivudine-entecavirresistant clone (L180M+M204V+S202G) [R. K. Rawal et al. 2'-Fluoro-6'-methylene-carbocyclic adenosine phosphoramidate (FMCAP) prodrug: In vitro anti-HBV activity against the lamivudineentecavir resistant triple mutant and its mechanism of action. *Bioorg. Med. Chem. Lett.* 2013. 23, 503-506.]. Furthermore, preparation of the corresponding 5'-phosphoramidate of FMCA resulted in a compound that was 10-fold more potent than FMCA against both the wild-type ($EC_{50}=0.62$ µM) and resistant mutant ($EC_{50}=0.054$ µM) [R. K. Rawal et al. 2'-Fluoro-6'-methylene-carbocyclic adenosine phosphoramidate (FMCAP) prodrug: In vitro anti-HBV activity against the lamivudineentecavir resistant triple mutant and its mechanism of action. *Bioorg. Med. Chem. Lett.* 2013. 23, 503-506.].

It is also known that the phosphoramidate conjugates of clevudine (EIDD-02173) retained potent anti-HBV activity in cell culture models of infection. The phosphoramidate moiety successfully delivered clevudine-5'-monophosphate to the liver while significantly decreasing non-liver organ exposure. Selective targeting of the liver could potentially lead to a decrease in the off-target effects related to clevudine in humans. [G. R. Bluemling et al. Targeted Delivery of Clevudine-5'-Monophosphate to the Liver After Oral Administration of a Clevudine-5'-Phosphoramidate Conjugate to Rats for the Treatment of HBV Infections. *Global Antiviral Journal* 2015, 11, Suppl. 3: HEP DART 2015: Abstr. 104, P. 97].

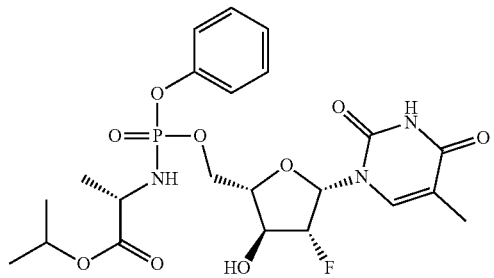

Gemcitabin-5'-phosphoramidate (NUC-1031) [M. Slusarczyk et al. Application of ProTide Technology to Gemcitabine: A Successful Approach to Overcome the Key Cancer Resistance Mechanisms Leads to a New Agent (NUC-1031) in Clinical Development. *J. Med. Chem.* 2014, 57, 1531-1542] showed a high anti-cancer activity. In particular NUC-1031 significantly reduced tumor volume in vivo in xenografts models of human pancreatic cancer. Important to note that activation of NUC-1031 is much less dependent on the nucleoside transporters and deoxycytidine than gemcitabine. In addition, NUC-1031 is resistant to cytidine deaminase degradation unlike gemcitabine.

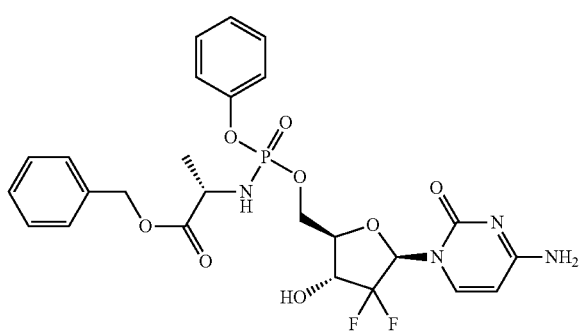

It should be noted that the structure of phosphoramidite moiety has a significant impact on the stability of phosphoramidate nucleosides in various media, their pharmacokinetics, bioavailability, distribution in body organs and the selectivity of their action [M. J. Sofia et al. 2010. P. Wang et al. Phosphoramidate prodrugs of (−)-β-D-(2R, 4R)-dioxolane-thymine (DOT) as potent anti-HIV agents. *Antiviral Chem. Chemotherapy* 2012, 22, 217-238. L. Bondada et al. Adenosine Dioxolane Nucleoside Phosphoramidates as Antiviral Agents for Human Immunodeficiency and Hepatitis B Viruses. *ACS Med. Chem. Lett.* 2013, 4, 747-751. M. Slusarczyk et al. Application of ProTide Technology to Gemcitabine: A Successful Approach to Overcome the Key Cancer Resistance Mechanisms Leads to a New Agent (NUC-1031) in Clinical Development. *J. Med. Chem.* 2014, 57, 1531-1542.].

So far synthesis of new phosphoramidate nucleosides and their use as chemotherapeutic agents for the treatment of viral diseases and cancer are highly relevant.

Is important to note also that until now nucleoside-containing macroheterocyclic phosphoramidates and their use for treating viral and cancerous diseases were unknown.

SUMMARY OF THE INVENTION

The present invention is directed toward novel macroheterocyclic nucleoside derivative and their analogue represented by the compounds of general formula 1, general formula 2, a stereoisomer, isotope-enriched analogue, pharmaceutically acceptable salt, hydrate, solvate, or crystalline or polymorphic form thereof, for the treatment of viral and cancerous diseases in mammals.

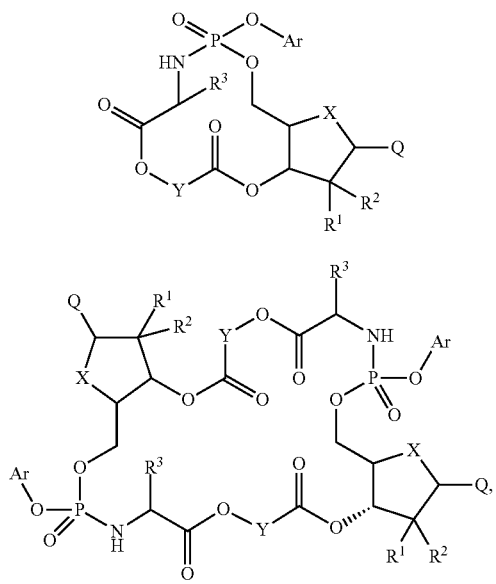

wherein:
Ar is aryl or hetaryl;
$R^1$ and $R^2$ are not necessarily the same substituents selected from H, F, Cl, $CH_3$, OH;
$R^3$ is H or $CH_3$;
X is oxygen or ethanediyl-1, 1 ($C=CH_2$);
Y is $CH(R^4)(CH_2)_k$, $CH(R^4)(CH_2)_mC(O)O(CH_2)_n$;
$R^4$ is H or $CH_3$;
k has a value from zero to six;
m has a value from zero to two;
n has a value of one to four;
Q is a radical selected from Q1-Q4;

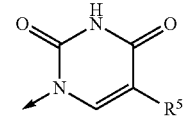

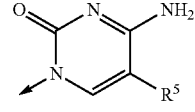

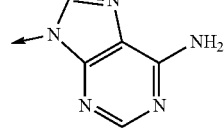

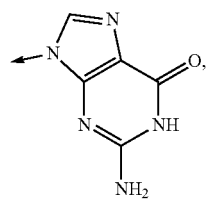

wherein: $R^5$ is the substituent selected from H, F, Cl, $CH_3$, OH;
the arrow (→) indicates the location, joined by Q1-Q4.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3Rd ed., John Wiley & Sons, 1999.

The term "heteroaryl," as used herein, refers to a mono- or polycyclic aromatic radical having one or more ring atom selected from S, O and N; and the remaining ring atoms are carbon. Heteroaryl includes, but is not limited to, pyridinyl, pyrazinyl, pyrimidinyl, quinolinyl, isoquinolinyl, benzimidazolyl, benzooxazolyl, or quinoxalinyl.

The term "alkyl" as used herein, refers to saturated, straight- or branched-chain hydrocarbon radicals containing from one to six carbon atoms. The examples of $C_1$-$C_6$ alkyl radicals include, but are not limited to, methyl, ethyl, propyl, isopropyl, n-butyl, and tert-butyl.

"Lower alkyl" refers to an unbranched or branched alkyl chain comprising 1-4 carbon atoms.

The term "alkoxy" refers to an —O-alkyl group or an —O-cycloalkyl group, wherein alkyl and cycloalkyl are as defined above. Examples of —O-alkyl groups include, but are not limited to, methoxy, ethoxy, n-propyloxy, i-propyloxy, n-butyloxy, i-butyloxy, t-butyloxy. "Lower alkoxy" as used herein denotes an alkoxy group with a "lower alkyl" group as previously defined. "$C_{1-10}$ alkoxy" refers to an —O-alkyl, wherein alkyl is $C_{1-10}$. Examples of —O-cycloalkyl groups include, but are not limited to, —O-cyclopropyl, —O-cyclobutyl, —O-cyclopentyl, and —O-cyclohexyl.

The term "cycloalkyl" as used herein, refers to carbocyclic ring system containing from 3 to six carbon atoms. The examples of $C_3$-$C_6$ cycloalkyl radicals include, but are not limited to, cyclopropyl, cyclobutyl, cyclopentyl, cyclohexyl.

The term "optionally substituted" means the group referred to can be substituted at one or more positions by any one or any combination of the radicals.

The term "N- and O-protecting group" or "protecting group" refers to those groups capable of protecting an amino or hydroxyl group against undesirable reactions. Commonly used protecting groups are described in Greene and Wuts, Protecting groups in chemical synthesis ($3^{rd}$ ed., John Wiley & Sons, NY (1999)). Non-limiting examples of N-protecting groups include acyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

"Active component" (drug substance) refers to a physiologically active compound of synthetic or other (biotechnological, vegetable, animal, microbicidal, and so on) origins exhibiting a pharmacological activity, which is an active ingredient of the pharmaceutical composition employed in production.

"Medicament" is a compound (or a mixture of compounds as a pharmaceutical composition) and a preparation of medicaments in the form of tablets, capsules, injections, ointments, and other ready forms intended for restoration, improvement, or modification of physiological functions in humans and animals and for the treatment and prophylaxis of diseases, for diagnostics, anesthesia, contraception, cosmetology, and so on.

"Therapeutic cocktail" represents a simultaneously administered combination of two or more medicaments exhibiting a different mechanism of pharmacological action and directed to various biotargets taking part in the disease process.

"Pharmaceutical composition" means a composition comprising a compound of general formula 2 and at least one component selected from a group consisting of pharmaceutically acceptable and pharmacologically compatible fillers, solvents, diluents, carriers, auxiliaries, distributors and excipients, delivery agents, such as preservatives, stabilizers, fillers, disintegrators, moisteners, emulsifiers, suspending agents, thickeners, sweeteners, flavouring agents, aromatizing agents, antibacterial agents, fungicides, lubricants, and prolonged delivery controllers, choice and suitable proportions of which depend on the nature and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacanth, and mixtures thereof.

Protection against microorganisms can be provided by various antibacterial and antifungal agents, such as, for example, parabens, chlorobutanole, sorbic acid, and similar compounds. Composition may also comprise isotonic agents, such as, for example, sugar, sodium chloride, and similar compounds. The prolonged effect of a composition may be achieved by agents slowing down the absorption of the active ingredient, for example, aluminum monostearate or gelatine. Examples of suitable carriers, solvents, diluents, and delivery agents include water, ethanol, polyalcohols and mixtures thereof, natural oils (such as olive oil), and organic esters (such as ethyl oleate) for injections. Examples of fillers are lactose, milk sugar, sodium citrate, calcium carbonate, calcium phosphate, and the like. The examples of disintegrators and distributors are starch, alginic acid and its salts, and silicates.

The examples of suitable lubricants are magnesium stearate, sodium lauryl sulfate, talc, and high molecular weight polyethylene glycol. A pharmaceutical composition for peroral, sublingual, transdermal, intramuscular, intravenous, subcutaneous, and local or rectal administration of the active ingredient, alone or in combination with another active compound, may be administered to humans and animals in standard administration form, or in a mixture with traditional pharmaceutical carriers. Suitable standard administration forms include peroral forms such as tablets, gelatin capsules, pills, powders, granules, chewing gums, and peroral solutions or suspensions; sublingual and transbuccal administration forms; aerosols; implants; local, transdermal, subcutaneous, intramuscular, intravenous, intranasal or intraocular forms, and rectal administration forms.

The compounds or salts of the present invention may also be used in the form of prodrugs.

The compounds of the invention may comprise asymmetrically substituted carbon and phosphorus atoms known as chiral centers. These compounds may exist, without limitation, as single stereoisomers or racemic mixtures. Compounds identified herein as single stereoisomers are meant to describe compounds that are present in a form that is substantially free from other stereoisomers (e.g., substantially free from other enantiomers or diastereomers). By "substantially free" it is meant that at least 80% of the compound in a composition is the described stereoisomer; preferably, at least 90% of the compound in a composition is the described stereoisomer; and, more preferably, at least 95%, 96%, 97%, 98%, or 99% of the compound in a composition is the described stereoisomer. Where the stereochemistry of a chiral carbon is not specified in the chemical structure of a compound, the chemical structure is intended to encompass compounds containing either stereoisomer of the chiral center. Individual stereoisomers of the compounds of this invention can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographic separation of the diastereomers and regeneration of the individual enantiomers, and enzymatic resolution.

Stereospecific synthesis typically involves the use of appropriate optically pure (enantiomerically pure) or substantially optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in a solution and loaded onto the column containing a chiral stationary phase. Enantiomers can then be separated by HPLC. The resolution of enantiomers can also be improved by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or a covalent bond with the chiral auxiliary. Non-limiting examples of suitable chiral auxiliaries include chirally pure amino acids, organic carboxylic acids, or organosulfonic acids. Once the diastereomers are separated by chromatography, individual enantiomers can be regenerated. Frequently, the chiral auxiliary can be recovered and used again.

Enzymes such as esterases, phosphatases, or lipases can be useful for the resolution of derivatives of enantiomers in an enantiomeric mixture. For example, an ester derivative of a carboxyl group in the compounds to be separated can be treated with an enzyme, which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treating the carboxylic acid with a suitable optically pure base, such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

In addition, where a compound exists in various tautomeric forms, a recited compound is not limited to any one specific tautomer, but rather is intended to encompass all tautomeric forms. The compounds of the invention may exist in different stable conformational forms, which may be separable. Torsional asymmetry due to restricted rotations about an asymmetric single bond, for example, because of steric hindrance or ring strain, may permit separation of different conformers. The invention encompasses each conformational isomer of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms.

The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms. If a linking element in a depicted structure is a bond, then the element left to the linking element is joined directly to the element right to the linking element via a covalent bond. If two or more adjacent linking elements in a depicted structure are bonds, then the element left to these linking elements is joined directly to the element right to these linking elements via a covalent bond.

When a chemical formula is used to describe a moiety, the dash(es) indicates the portion of the moiety that has the free valence(s). If a moiety is described as being "optionally substituted", the moiety may be either substituted or unsubstituted. If a moiety is described as being optionally substituted with up to a particular number of non-hydrogen radicals, said moiety may be either unsubstituted, or substituted by up to that particular number of non-hydrogen radicals, or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions.

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g., a reduction in viral load.

The term "prodrug" refers to derivatives of the compounds of the invention which have chemically or metabolically cleavable groups and become, by solvolysis or under physiological conditions, the compounds of the invention, which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals (see, Bungard, H., Design of products, pp. 7-9, 21-24, Elsevier, Amsterdam 1985). Prodrugs include acid derivatives well known to practitioners in the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to a physical association of a compound of this invention with one or more solvent molecules, whether organic or inorganic. This physical association often includes hydrogen bonding. In certain instances, the solvate will be capable of isolation, for example, when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The present disclosure will now be described in connection with certain embodiments, which are not intended to limit its scope. On the contrary, the present disclosure covers all alternatives, modifications, and equivalents as can be included within the scope of the claims. Thus, the following examples, which include specific 10 embodiments, will illustrate one practice of the present disclosure, it being understood that the examples are for the purposes of illustration of certain embodiments and are presented to provide what is believed to be the most useful and readily understood description of its procedures and conceptual aspects.

DETAILED DESCRIPTION OF THE INVENTION

One embodiment of the present invention is a novel macroheterocyclic nucleoside derivative and its analogue of the general formula 1 or general formula 2, a stereoisomer, isotope-enriched analogue, pharmaceutically acceptable salt, hydrate, solvate, or crystalline or polymorphic form thereof,

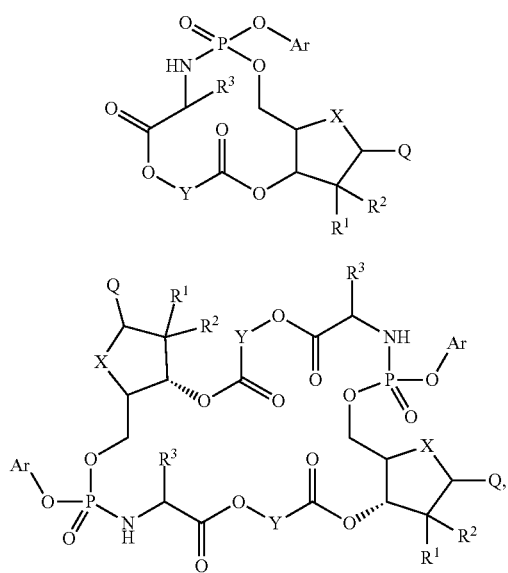

wherein:
Ar is aryl or hetaryl;
$R^1$ and $R^2$ are not necessarily the same substituents selected from H, F, Cl, $CH_3$, OH;
$R^3$ is H or $CH_3$;
X is oxygen or ethanediyl-1, 1 ($C\!=\!CH_2$);
Y is $CH(R^4)(CH_2)_k$, $CH(R^4)(CH_2)_m C(O)O(CH_2)_n$;
$R^4$ is H or $CH_3$;
k has a value from zero to six;
m has a value from zero to two;
n has a value of one to four;
Q is a radical selected from Q1-Q4;

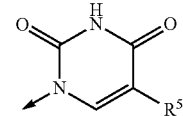
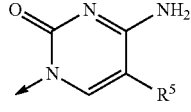
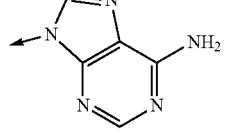
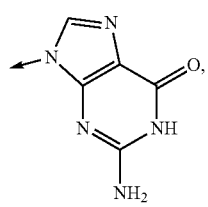

wherein: $R^5$ is the substituent selected from H, F, Cl, $CH_3$, OH;
the arrow (→) indicates the location, joined by Q1-Q4.

More preferred macroheterocyclic nucleoside derivatives and its analogue are: (2R,3aS,6S,9S,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(1/2)), (2R,3aS,6S,9S,11R,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(2)), (2R,3aS,6S,9S,11R,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(2)), (2R,3R,3aR,6S,9S,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(3/4)), (2R,3R,3aR,6S,9S,11S,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(3)), (2R,3R,3aR,6S,9S,11R,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(4)), (2R,3R,3aR,10S,14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(5/6)), (2R,3R,3aR,10S,12S,14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(5)), (2R,3R,3aR,10S,12R,14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(6)), (2S,3aS,11S,15aR)-2-(2-amino-6-oxo-1,6-dihydro-purin-9-yl)-11-methyl-1-methylene-13-oxo-13-phenoxy-decahydro-4,9, 14-trioxa-12-aza-13-phospha-cyclopentacyclotetradecene-5,10-dione (1(7/8)), (2S,3aS,11S,13S,15aR)-2-(2-amino-6-oxo-1,6-dihydro-purin-9-yl)-11-methyl-1-methylene-13-oxo-13-phenoxy-decahydro-4,9,14-trioxa-12-aza-13-phospha-cyclopentacyclotetradecene-5,10-dione (1(7)), (2S,3S,3aS,11S,13R,15aR)-2-(6-amino-purin-9-yl)-3,11-dimethyl-1-methylene-13-oxo-13-phenoxy-decahydro-4,9,14-trioxa-12-aza-13-phospha-cyclopentacyclotetradecene-5,10-dione (1(8)), (2R,3aS,11S,15aR)-2-(2,4-dioxo-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(9/10)), (2R,3aS,11S,13S,15aR)-2-(2,4-dioxo-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(9)), (2S,3aR,11S,13R,15aS)-11-methyl-2-(5-methyl-2,4-dioxo-3,4-dihydro-2H-pyrimidin-1-yl)-13-oxo-13-phenoxy-octahydro-1,4,9,14-tetraoxa-12-aza-13-phospha-cyclopentacyclotetradecene-5,10-dione (1(10)), (2R,3aS,11S,15aR)-2-(2,4-dioxo-5-trifluoromethyl-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(11/12)), (2R,3aS,11S,13S,15aR)-2-(2,4-dioxo-5-trifluoromethyl-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(11)), (2S,3R,3aS,11S,13R,15aS)-3-fluoro-11-methyl-2-(5-methyl-2,4-dioxo-3,4-dihydro-2H-pyrimidin-1-yl)-13-oxo-13-phenoxy-octahydro-1,4,9,14-tetraoxa-12-aza-13-phospha-cyclopentacyclotetradecene-5,10-dione (1(12)), (2R,3R,3aR,11S,5aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(13/14)), 2R,3R,3aR,11S,13S,15aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(13)), (2R,3R,3aR,11S,13R,15aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(14)), (2R,3aR,11S,15aR)-2-(4-amino-2-oxo-2H-pyrimidin-1-yl)-3,3-difluoro-11-methyl-13-oxo-13-phenoxy-octahydro-1,4,9,14-tetraoxa-12-aza-13-phospha-cyclopentacyclotetradecene-5,10-dione (1(15/16)), (2R,3aR,11S,13S,15aR)-2-(4-amino-2-oxo-2H-pyrimidin-1-yl)-3,3-difluoro-11-methyl-13-oxo-13-phenoxy-octahydro-1,4,9,14-tetraoxa-12-aza-13-phospha-cyclopentacyclotetradecene-5,10-dione (1(15)), (2R,3aR,11S,13R,15aR)-2-(4-amino-2-oxo-2H-pyrimidin-1-yl)-3,3-difluoro-11-methyl-13-oxo-13-phenoxy-octahydro-1,4,9,14-tetraoxa-12-aza-13-phospha-cyclopentacyclotetradecene-5,10-dione (1(16)), (2R,3R,3aR,12S,16aR)-2-(2,4-dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(17/18)), (2R,3R,3aR,12S,14S,16aR)-2-(2,4-dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(17)), (2R,3R,3aR,12S,14R,16aR)-2-(2,4-dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(18)), (2R,3R,3aR,13S,15S,17aR)-2-(2,4-dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(19/20)), (2R,3R,3aR,13S,15S,17aR)-2-(2,4-dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(19)), (2R,3R,3aR,13S,15R,17aR)-2-(2,4-dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(20)), (2R,3R,3aR,14S,16S,18aR)-2-(2,4-dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cycloheptadecene-5,13-dione (1(21/22)), (2R,3R,3aR,14S,16S,18aR)-2-(2,4-dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cyclopentacycloheptadecene-5,13-dione (1(21)), (2R,3R,3aR,14S,16R,18aR)-2-(2,4-dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cyclopentacycloheptadecene-5,13-dione (1(22)), (2R,3R,3aR,15S,17S,19aR)-2-(2,4-dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(23/24)), (2R,3R,3aR,15S,17S,19aR)-2-(2,4-dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(23)), (2R,3R,3aR,15S,17R,19aR)-2-(2,4-dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(24)), (2R,3R,3aR,12S,15S,17S,19aR)-2-(2,4-dioxo-3,4-dihydro-2H-pyrimidin-1-yl)-3-fluoro-3,12,15-trimethyl-17-oxo-17-phenoxy-decahydro-1,4,9,13,18-pentaoxa-16-aza-17-phospha-cyclopentacyclooctadecene-5,10,14-trione (1(25/26)), (2R,3R,3aR,12S,15S,17S,19aR)-2-(2,4-dioxo-3,4-dihydro-2H-pyrimidin-1-yl)-3-fluoro-3,12,15-trimethyl-17-oxo-17-phenoxy-decahydro-1,4,9,13,18-pentaoxa-16-aza-17-phospha-cyclopentacyclooctadecene-5,10,14-trione (1(25)), (2R,3R,3aR,15S,17R,19aR)-2-(2,4-dioxo-3,4-dihydro-2H-pyrimidin-1-yl)-3-fluoro-3,15-dimethyl-17-oxo-17-phenoxy-decahydro-1,4,8,13,18-pentaoxa-16-aza-17-phospha-cyclopentacyclooctadecene-5,9,14-trione (1(26)), (2R,3R,3aR,9S,11S,13aR,15R,16R,16aR,22S,24S,26aR)-2,15-bis(2,4-dioxo-3,4-dihydropyrimidin-1(2H)-yl)-3,16-difluoro-3,9,16,22-tetramethyl-11,24-diphenoxydodecahydro-2H,13H-difuro[3,2-j:3',2'-v][1,6,9,13,18,21,3,15,2,14]hexaoxadiazadiphosphacyclotetracosine-5,8,18,21(6H,9H,19H,22H)-tetrone 11,24-dioxide (1(27)), (2R,3R,3aR,11S,13S,15aR,17R,18R,18aR,26S,28S,30aR)-2,17-bis(2,4-dioxo-3,4-dihydropyrimidin-1(2H)-yl)-3,18-difluoro-3,11,18,26-tetramethyl-13,28-diphenoxyhexadecahydro-2H,15H-difuro[3,2-1:3',2'-z][1,6,11,15,20,25,3,17,2,16]hexaoxadiazadiphosphacyclooctacosine-5,10,20,25(6H,11H,21H,26H)-tetrone 13,28-dioxide (1(28)), or a stereoisomer, isotope-enriched analogue, pharmaceutically acceptable salt, hydrate, solvate, or crystalline or polymorphic form thereof.

1(1/2)
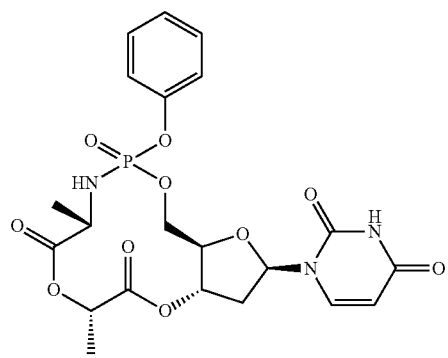
1(1)
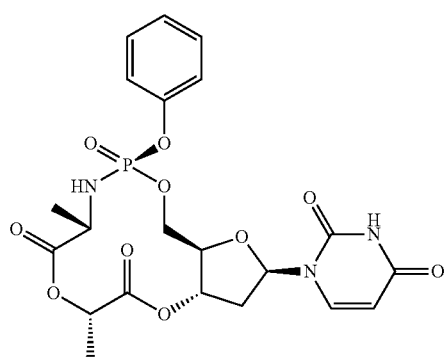
1(2)
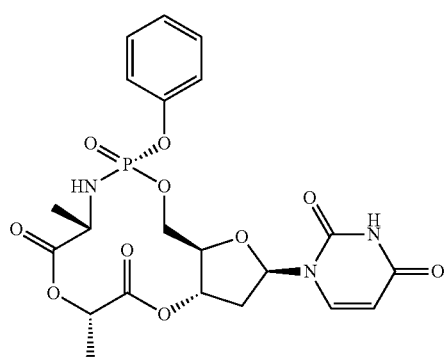
1(3/4)
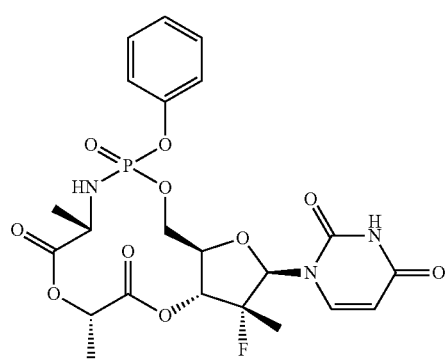
-continued
1(3)
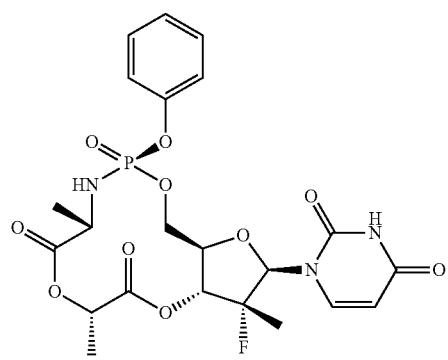
1(4)
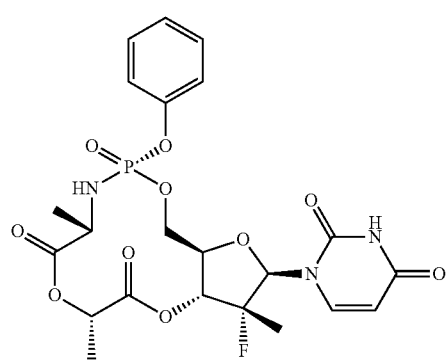
1(5/6)
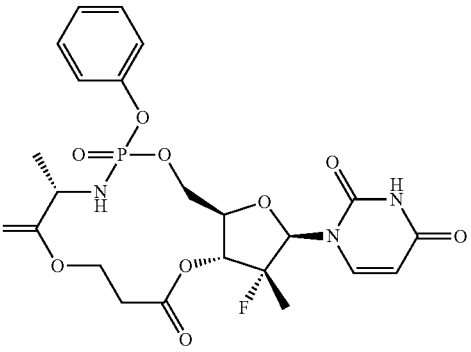
1(5)
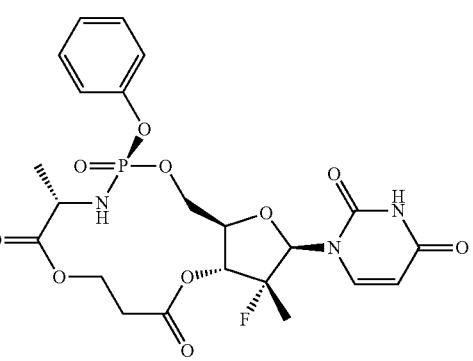

1(6)
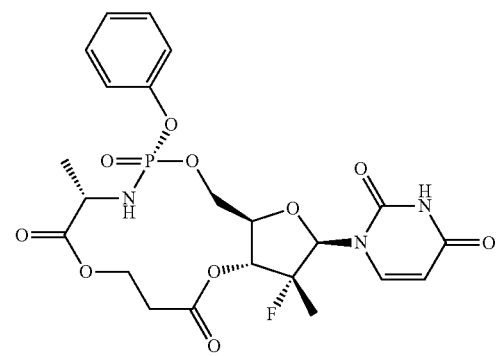
1(7/8)
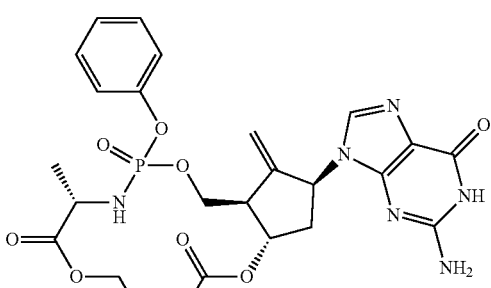
1(7)
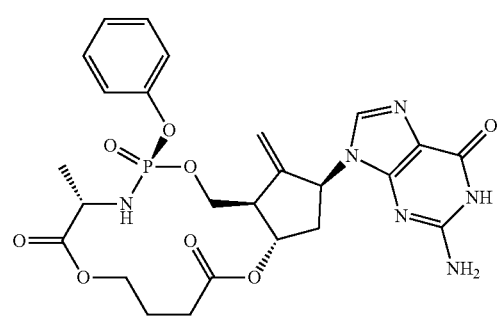
1(8)
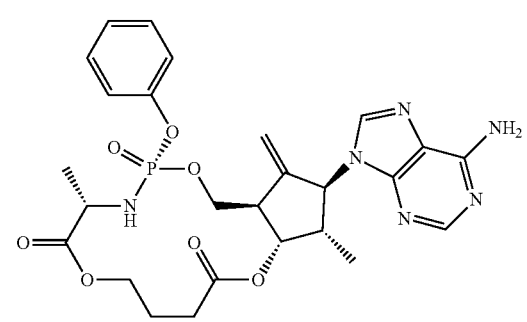
1(9/10)
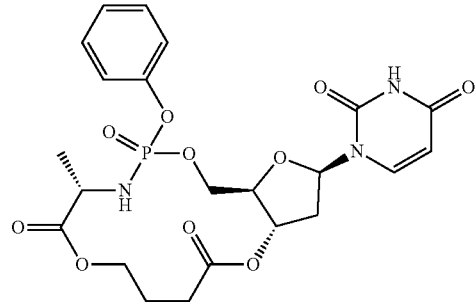
1(9)
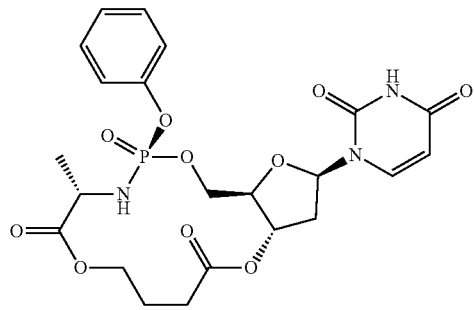
1(10)
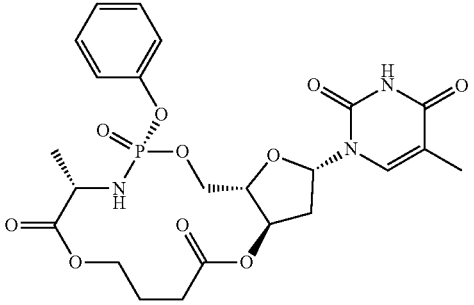
1(11/12)
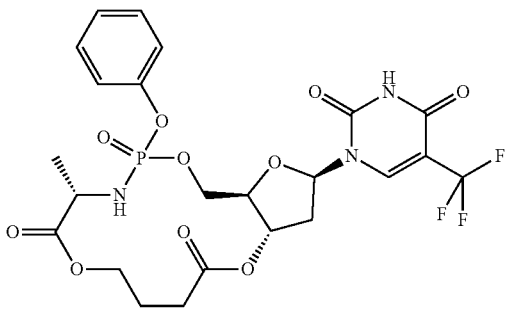
1(11)
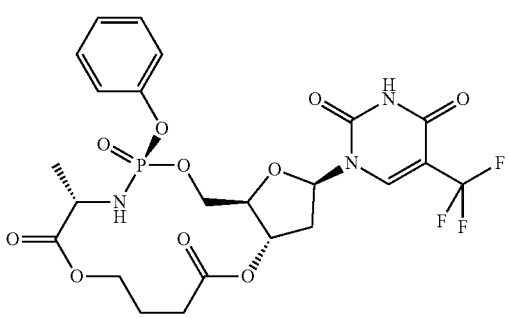
1(12)
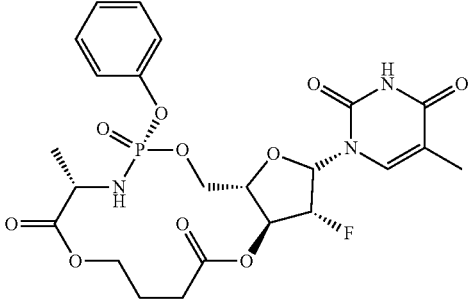

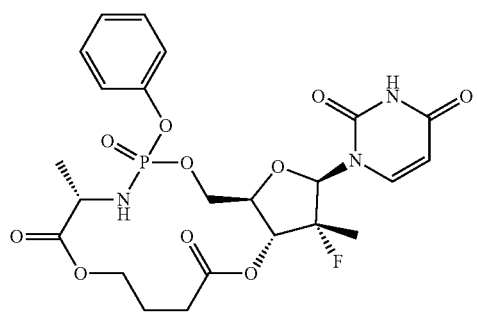
1(13/14)
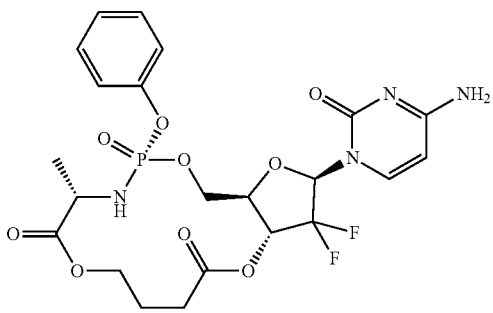
1(16)
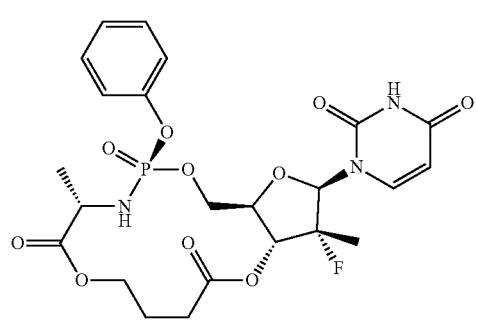
1(13)
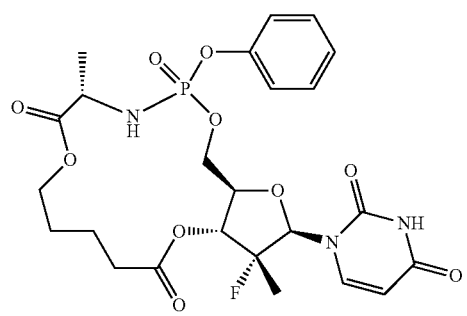
1(17/18)
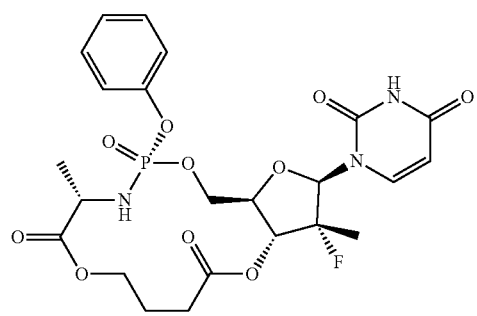
1(14)
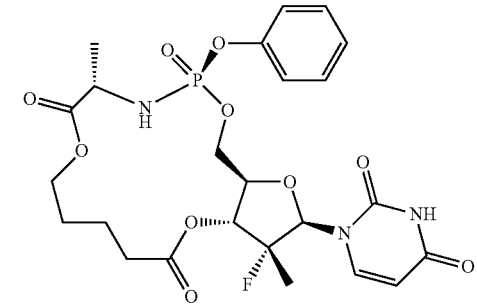
1(17)
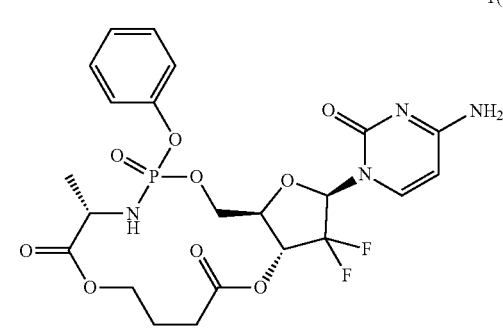
1(15/16)
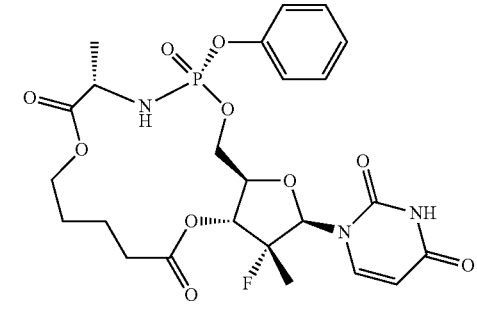
1(18)
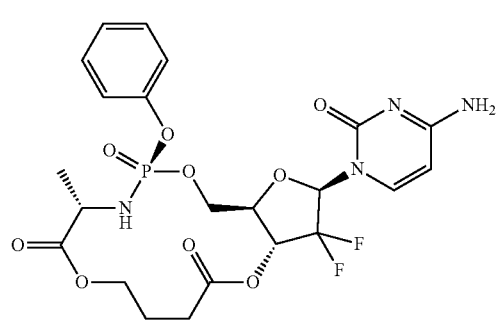
1(15)
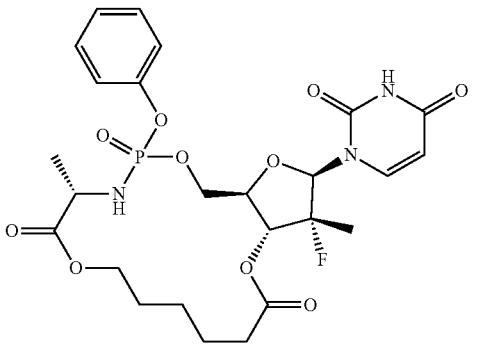
1(19/20)

1(19)
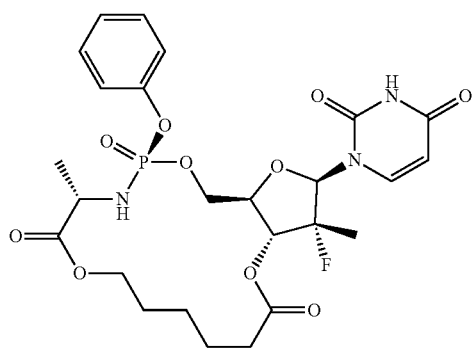
1(20)
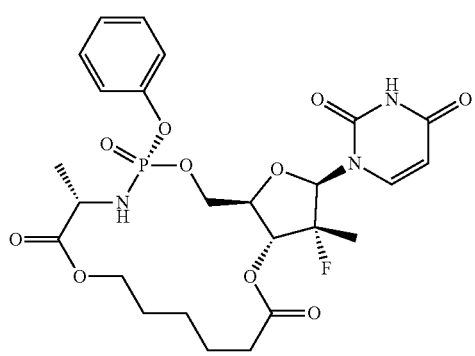
1(21/22)
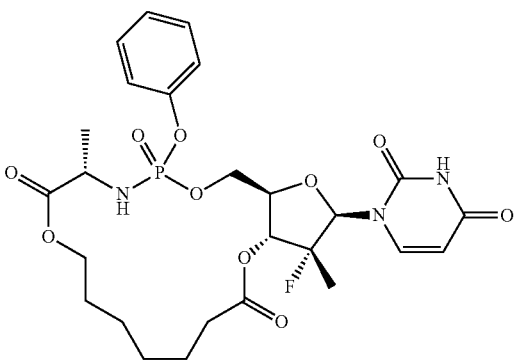
1(21)
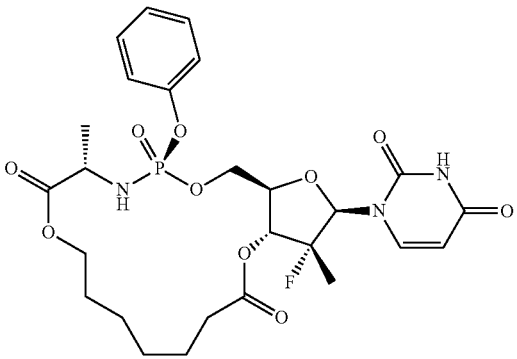
1(22)
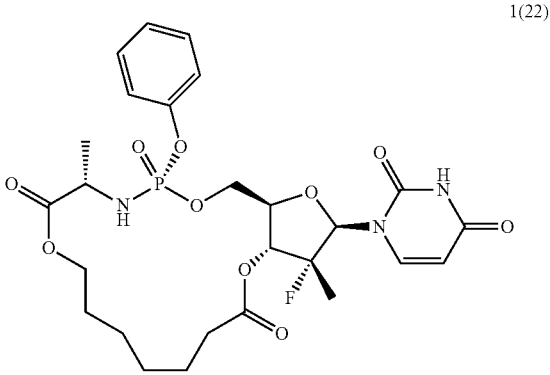
1(23/24)
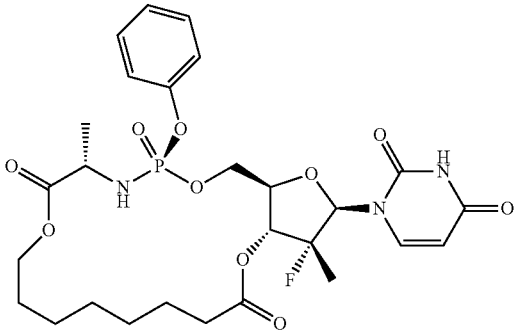
1(23)
1(24)
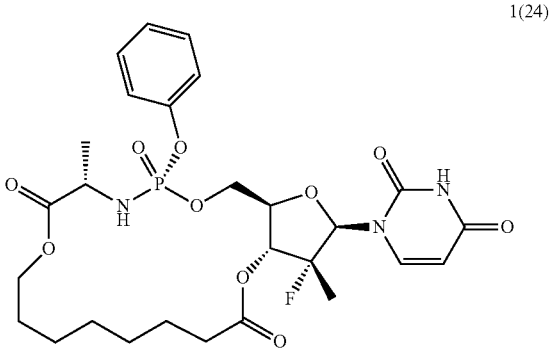

1(25/26)

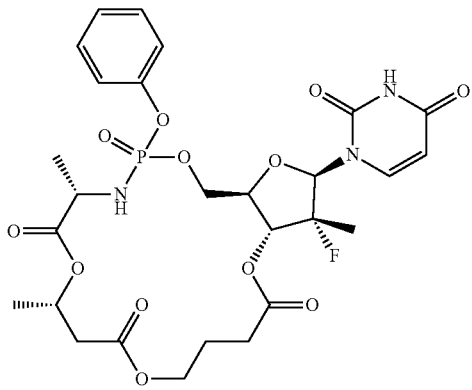

1(28)

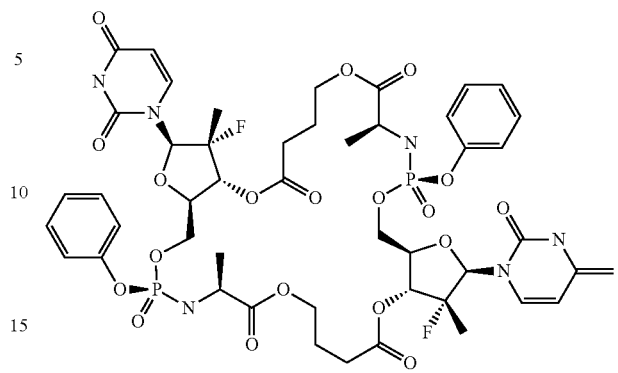

1(25)

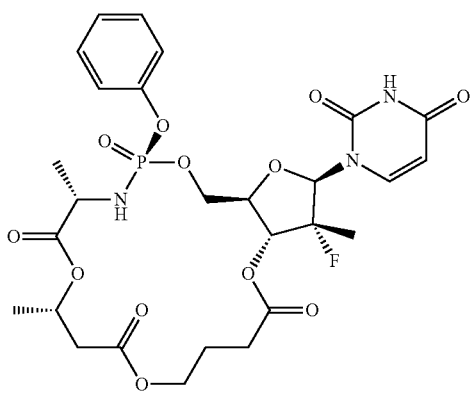

1(26)

1(27)

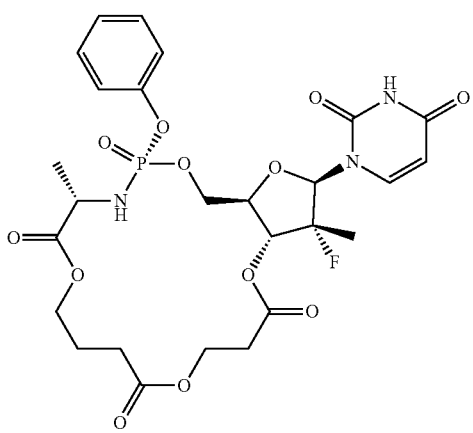

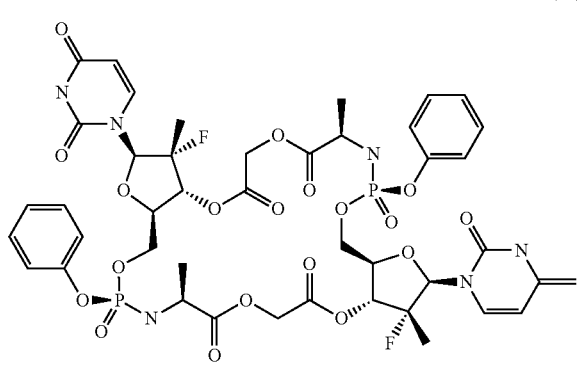

New macroheterocyclic nucleoside derivatives and their analogues of the general formula 1 or general formula 2 are undoubtedly of interest in particular as drug candidates for the treatment of hepatitis C. For example, macroheterocycle 1(13) is more stable ($T_{1/2}$>24 h) in the simulated gastric fluid (SFG) and the human S9 fraction ($T_{1/2}$>12.4 h) than Sovaldi®, for which the $T_{1/2}$=15 h in SGF environment and $T_{1/2}$>1.8 h in Human S9 fraction.

Macroheterocycle 1(13) also shows higher $C_{max}$=341 ng/ml metabolite of PSI-352707 [E. Murakami et al. Mechanism of activation of PSI-7851 and its diastereoisomer PSI-7977. J. Biol. Chem. 2010, 285 (45), 34337-34347] in plasma of rats (SD rats, 10 mg/kg p.o.) than under the same conditions shows Sovaldi®, for which $C_{max}$=154 ng/ml metabolite PSI-352707, with the same time (1 h) to achieve a comparable $C_{max}$ and enter values $T_{1/2}$=1.80 h and $T_{1/2}$=1.75 h, respectively, for Macroheterocycle 1(13) and Sovaldi®. In rat liver Cmax of PSI-352707 is comparable for macroheterocycle 1(13) and Sovaldi®, respectively $C_{max}$=1578 ng/ml and $C_{max}$=1702 ng/ml. Meanwhile macroheterocycle 1(13) has a more acceptable value $T_{max}$=0.25 h and $T_{1/2}$=1.9 h than Sovaldi®, for which $T_{max}$=0.50 h and $T_{1/2}$=1.3 h.

Dosage, Administration, and Use

The subject of the present invention is a pharmaceutical composition comprising one or more of macroheterocyclic nucleoside derivatives of general formula 1 or general formula 2, a stereoisomer, isotope-enriched analogue, pharmaceutically acceptable salt, hydrate, solvate, or crystalline or polymorphic form thereof, optionally in combination with a pharmaceutically acceptable excipient, carrier, additive, diluent, and equivalent medium for the treatment of viral infections and/or neoplastic diseases in mammals.

The compounds of general formula 1 or 2 may be formulated in a wide variety of oral administration dosage forms and carriers, oral administration can be in the form of tablets, coated tablets, hard and soft gelatin capsules, solutions, emulsions, syrups, or suspensions. Compounds of the present invention are efficacious when administered by suppository administration, among other routes of administration. The most convenient manner of administration is generally oral using a convenient daily dosing regimen which can be adjusted according to the severity of the disease and the patient's response to the antiviral and anticancer medication.

A macroheterocyclic nucleoside derivatives of general formula 1 or general formula 2, a stereoisomer, isotope-enriched analogue, pharmaceutically acceptable salt, hydrate, solvate, or crystalline or polymorphic form thereof, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

Solid form preparations include powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous materials such as natural or synthetic gums, resins, methylcellulose, sodium carboxymethylcellulose, and other well known suspending agents.

The macroheterocyclic nucleoside derivative of general formula 1 or general formula 2, a stereoisomer, isotope-enriched analogue, pharmaceutically acceptable salt, hydrate, solvate, or crystalline or polymorphic form thereof, may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The macroheterocyclic nucleoside derivative of general formula 1 or general formula 2, a stereoisomer, isotope-enriched analogue, pharmaceutically acceptable salt, hydrate, solvate, or crystalline or polymorphic form thereof, may be formulated for vaginal administration. Pessaries, tampons, creams, gels, pastes, foams or sprays containing in addition to the active ingredient such carriers as are known in the art to be appropriate The subject of the invention is directed to a use of the macroheterocyclic nucleoside derivative represented by formula 1 or general formula 2, a stereoisomer, isotope-enriched analogue, pharmaceutically acceptable salt, hydrate, solvate, or crystalline or polymorphic form thereof, in the manufacture of a medicament for the treatment of viral and cancerous diseases. It is contemplated that the compound of the use of the macroheterocyclic nucleoside derivative represented by formula 1 or general formula 2 in the manufacture of a medicament for the treatment of any of the antiviral and anticancer conditions disclosed herein can be any of the compounds of the formulas 1(1)-1(26), 2(1), and 2(2), a stereoisomer, isotope-enriched analogue, pharmaceutically acceptable salt, hydrate, solvate, or crystalline or polymorphic form thereof, either alone or in combination with another compound of the present invention. A medicament includes, but is not limited to, any one of the compositions contemplated of the present invention.

The term "medicament" means a substance used in a method of treatment and/or prophylaxis of a subject in need thereof, wherein the substance includes, but is not limited to, a composition, a formulation, a dosage form, and the like, comprising the phosphoramidate macroheterocycle of formula 1 or general formula 2.

The subject of the present invention is directed to a method of treatment and/or prophylaxis in a subject in need thereof said method comprises administering a therapeutically effective amount of the macroheterocyclic nucleoside derivative represented by formula 1 or general formula 2, a stereoisomer, isotope-enriched analogue, pharmaceutically acceptable salt, hydrate, solvate, or crystalline or polymorphic form thereof to the subject.

The subject of the present invention is also directed to a method of treatment and/or prophylaxis in a subject in need thereof said method comprises administering a therapeutically effective of at least two or more different macroheterocyclic nucleoside derivatives falling within the scope of the compound represented by formula 1 or general formula 2, a stereoisomer, isotope-enriched analogue, pharmaceutically acceptable salt, hydrate, solvate, or crystalline or polymorphic form thereof to the subject.

The subject of the present invention is also directed to a method of treatment and/or prophylaxis in a subject in need thereof said method comprises alternatively or concurrently administering a therapeutically effective of at least two macroheterocyclic nucleoside derivatives falling within the scope of the compound represented by formula 1 or general formula 2, a stereoisomer, isotope-enriched analogue, pharmaceutically acceptable salt, hydrate, solvate, or crystalline or polymorphic form thereof to the subject.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the sixth embodiment can be any of the compounds contemplated in any of the aspects of the first, second, and third embodiments or those specifically recited in the tables above, either alone or in combination with another compound of the present invention.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.1 and about 10 g, including all values in between, per day should be appropriate in monotherapy and/or in combination therapy. A preferred daily dosage is between about 0.1 and about 7 g per day, more preferred 0.2 and about 5.0 g per day. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The subject of the present invention is directed to a method of treatment and/or prophylaxis in a subject in need thereof said method comprises administering to the subject a therapeutically effective of a compound represented by formula 1 or general formula 2, a stereoisomer, isotope-enriched analogue, pharmaceutically acceptable salt, hydrate, solvate, or crystalline or polymorphic form thereof, and a therapeutically effective amount of another antiviral agent; wherein the administration is concurrent or alternative. It is understood that the time between alternative administration can range between 1-24 hours, which includes any sub-range.

Examples of "another antiviral agents" include, but are not limited to: HCV NS3 protease inhibitors Examples of "another antiviral agents" include, but are not limited to: HCV NS3 protease inhibitors, HCV NS4 inhibitors (see US US 20140296136, U.S. Pat. Nos. 8,987,195, 7,973,040, US 2012214783); HCV NS4 inhibitors (see EP1497282); HCV NS3/NS4 inhibitors (EP 2364984); HCV NS5A inhibitors (Shingo Nakamoto et al. Hepatitis C virus NS5A inhibitors and drug resistance mutations. *World J Gastroenterol.* 2014 Mar. 21; 20(11): 2902-2912 (http://www.ncbi.nlm.nih.gov/pmc/articles/PMC3961994/); A. V. Ivachtchenko et al. Discovery of Novel Highly Potent Hepatitis C Virus NS5A Inhibitor (AV4025). *J. Med. Chem.* 2014, 57, 7716-7730; Pat. Appl. U.S. Ser. No. 14/845,333); toll-like receptor agonists (see WO 2015023958, WO 2012097012); and other inhibitors (see WO 2014106019, WO 2014033176, WO 2014033170, WO 2014033167, WO 2013006394, US 20090163545).

More preferred is a pharmaceutical composition, which together with the novel macroheterocyclic nucleoside derivative represented by formula 1 or general formula 2, a stereoisomer, isotope-enriched analogue, pharmaceutically acceptable salt, hydrate, solvate, or crystalline or polymorphic form thereof, further includes an antiviral or anticancer drug in therapeutically effective amounts.

More preferred is a pharmaceutical composition, which together with the macroheterocyclic nucleoside derivative represented by formula 1 and general formula 2, a stereoisomer, isotope-enriched analogue, pharmaceutically acceptable salt, hydrate, solvate, or crystalline or polymorphic form thereof, further comprises a therapeutically effective amount the HCV NS5A ingibitor the selected from the group of Daclatasvir (Daklinza, BMS790052) [Belema, M. et al. *J. Med. Chem.* 57, 1643-1672, 2014, WO 2008/021927, WO 2008/021928, WO-2008/021936. https://en.wikipedia.org/wiki/Daclatasvir;], Ombitasvir (ABT-267) [DeGoey, et al. *J Med. Chem.* 57, 2047-2057, 2014, WO 2010/144646], GS-5885[ ], Velpatasvir (GS-5816) [Everson G. T. et al. Sofosbuvir with Velpatasvir in Treatment-Naive Noncirrhotic Patients with Genotype 1 to 6 Hepatitis C Virus Infection: A Randomized Trial. *Ann. Intern. Med.* 2015, 163(11), 818-826. doi: 10.7326/M15-1000. Epub 2015 Nov. 10. www.medkoo.com/products/9855], Odalasvir (ACH-3102) [U.S. Pat. No. 8,809,313. http://en.wikipedia.org/wiki/Odalasvir] and Elbasvir (MK-8742) [Coburn, C. A. et al. *ChemMedChem.* 8, 1930-1940, 2013, WO 2012/040923, WO 2012/041014], Hepavivir (AV-4025) [Ivachtchenko, A. V. et al. *J. Med. Chem.* 57, 7716-7730, 2014, WO 2012/074437, http://allachem.com/wp-content/uploads/2013/08/hcv-AV4025-082413.doc], AV-4067 and AV-4084 [Pat. Appl. U.S. Ser. No. 14/845,333.], AVI-4056 and AVI-4058 [Pat. Appl. US 15221613].

The subject of the present invention is directed to a method of treatment of viral and cancerous diseases in a subject in need thereof said method comprises alternatively or concurrently administering a therapeutically effective of a compound represented by general formula 1 or general formula 2, a stereoisomer, isotope-enriched analogue, pharmaceutically acceptable salt, hydrate, solvate, or crystalline or polymorphic form thereof, and another antiviral or anticancer agent to the subject. It is understood that the time between alternative administration can range between 1-24 hours, which includes any sub-range in between.

The subject of the present invention is directed to a method of treatment and/or prophylaxis in a subject in need thereof said method comprises administering to the subject a therapeutically effective of at least one compound represented by general formula 1 or general formula 2, a stereoisomer, isotope-enriched analogue, pharmaceutically acceptable salt, hydrate, solvate, or crystalline or polymorphic form thereof, and a therapeutically effective amount of another antiviral or anticancer agent; wherein the administration is concurrent or alternative. It is understood that the time between alternative administration can range between 1-24 hours, which includes any sub-range in between.

It is contemplated that the another antiviral agent includes, but is not limited to interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor, and a HBV DNA polymerase inhibitor and a HIV-1 reverse transcriptase (RT) inhibitor. When the active compound or its derivative or salt are administered in combination with another antiviral or anticancer agent the activity may be increased over the parent compound. When the treatment is combination therapy, such administration may be concurrent or sequential with respect to a compound represented by general formula 1 or general formula 2, a stereoisomer, isotope-enriched analogue, pharmaceutically acceptable salt, hydrate, solvate, or crystalline or polymorphic form thereof "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a viral infection, as used herein, also includes treatment or prophylaxis of a disease or a condition associated with or mediated by viral infection, or the clinical symptoms thereof.

Process for Preparation

The subject of the present invention is a process for preparing the macroheterocyclic nucleoside derivative represented by general formula 1 and general formula 2 by cyclization of acid of general formula 3 (Scheme 1) and if necessary division of the latter on the stereoisomers.

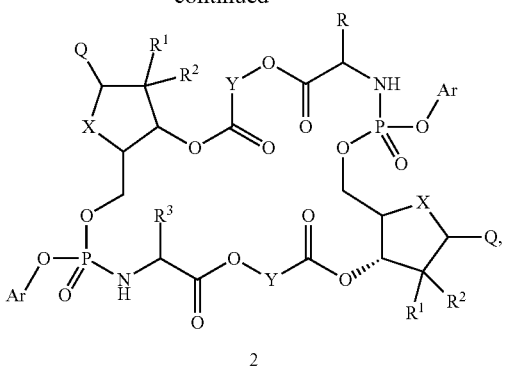

wherein: 1-3, and a stereoisomer, isotope-enriched analogue, pharmaceutically acceptable salt, hydrate, solvate, or crystalline or polymorphic form thereof; Ar, $R^1$, $R^2$, $R^3$, $R^4$, X, Y, and Q are as defined above.

Acids of general formula 3 can be obtained (Scheme 2) by reacting a corresponding chlorophosphorylamino derivative of general formula 8, a stereoisomer, isotope-enriched analogue, pharmaceutically acceptable salt, hydrate, solvate, or crystalline or polymorphic form thereof, with compound of general formula 12, a stereoisomer, isotope-enriched analogue, pharmaceutically acceptable salt, hydrate, solvate, or crystalline or polymorphic form thereof, followed by removal of the benzyl and Cbz groups by catalytic hydrogenation of the resulting benzyl ethers of general formula 13, a stereoisomer, isotope-enriched analogue, pharmaceutically acceptable salt, hydrate, solvate, or crystalline or polymorphic form thereof, and if necessary division of the latter on the stereoisomers.

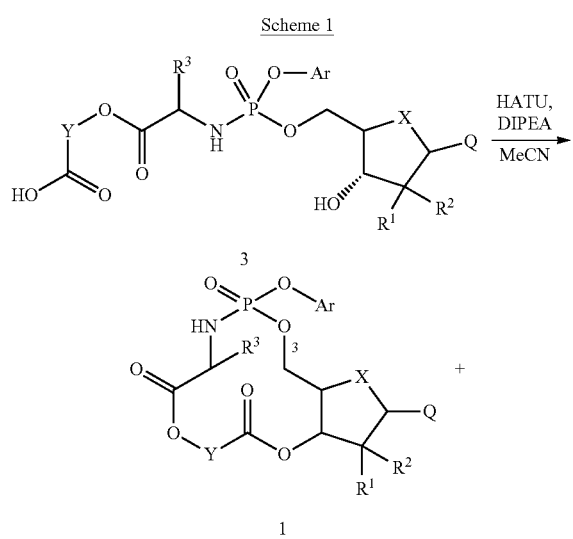

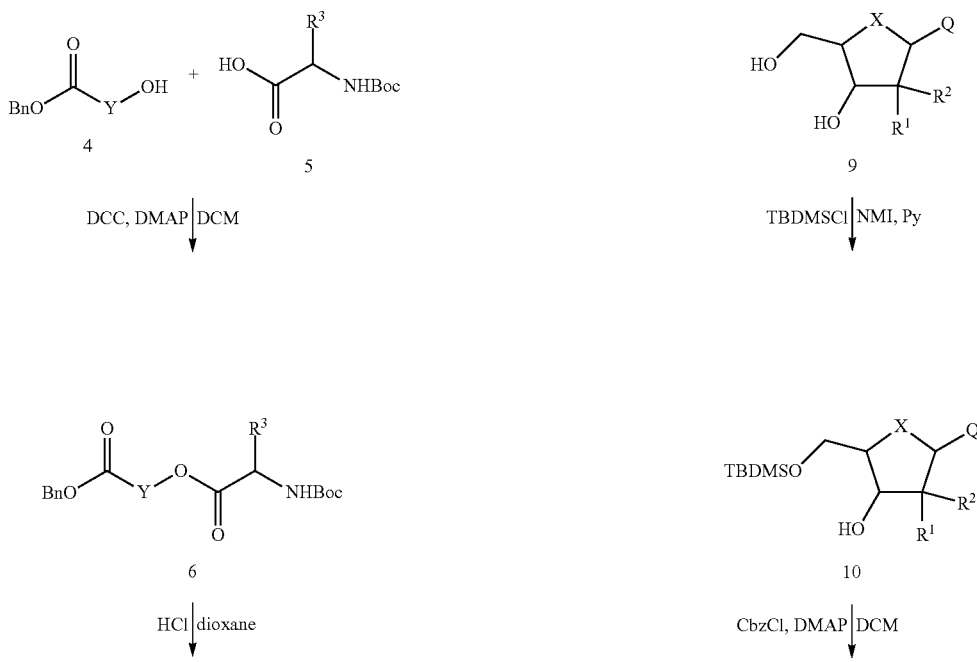

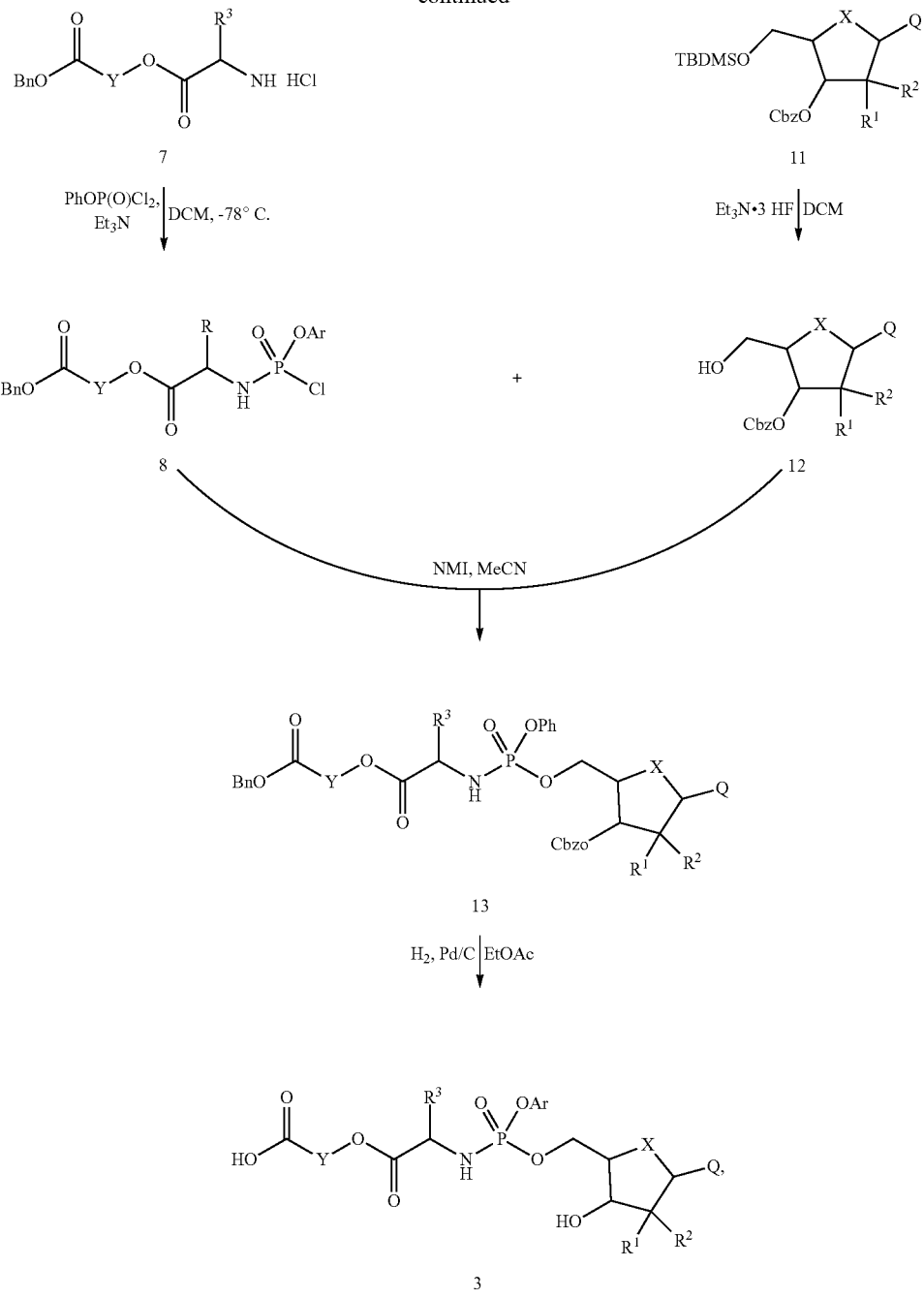

wherein: 3-13 and a stereoisomer, isotope-enriched analogue, pharmaceutically acceptable salt, hydrate, solvate, or crystalline or polymorphic form thereof; Ar, $R^1$, $R^2$, $R^3$, X, Y, and Q are as defined above.

Macroheterocyclic nucleoside derivative represented by general formula 1 or general formula 2 can be obtained starting from the acid of general formula 16 and if necessary division of the latter on the stereoisomers. The acid of general formula 16, a stereoisomer, isotope-enriched analogue, pharmaceutically acceptable salt, hydrate, solvate, or crystalline or polymorphic form thereof, can be obtained starting from the nucleoside of general formula 14 (Scheme 3).

Scheme 3

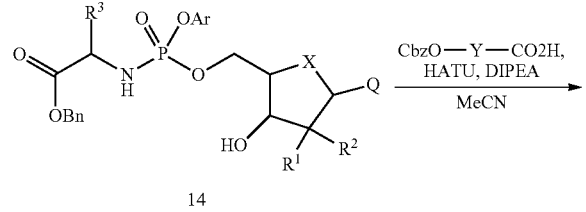

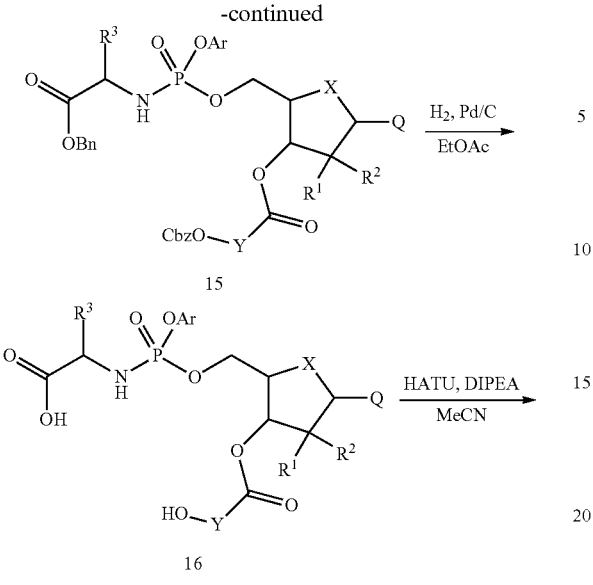

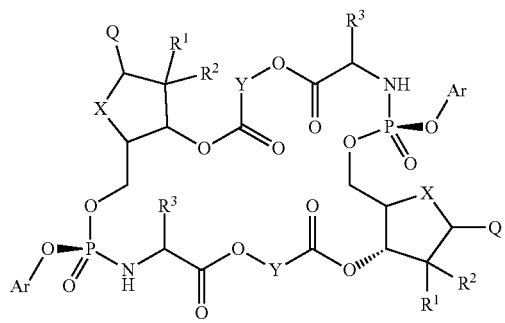

wherein: 14-16 and a stereoisomer, isotope-enriched analogue, pharmaceutically acceptable salt, hydrate, solvate, or crystalline or polymorphic form thereof; Ar, $R^1$, $R^2$, $R^3$, X, Y, and Q are as defined above.

For obtain certainly (S) and (R) phosphoric enantiomer of the macrocycles 1 and 2 ($1(P^{(S)})$, $2(P^{(S)})$, $1(P^{(R)})$, $2(P^{(R)})$) are using an appropriate (S) and (R) phosphoric enantiomers of corresponding acids of general formula $19(P(^S))$ or $19(P(^R))$ (Scheme 4).

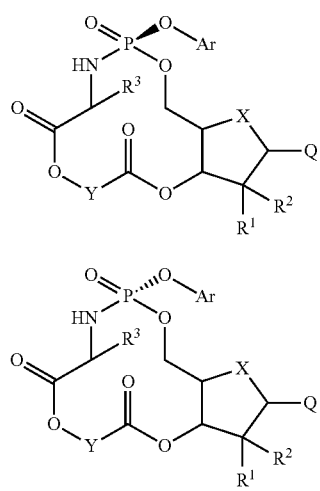

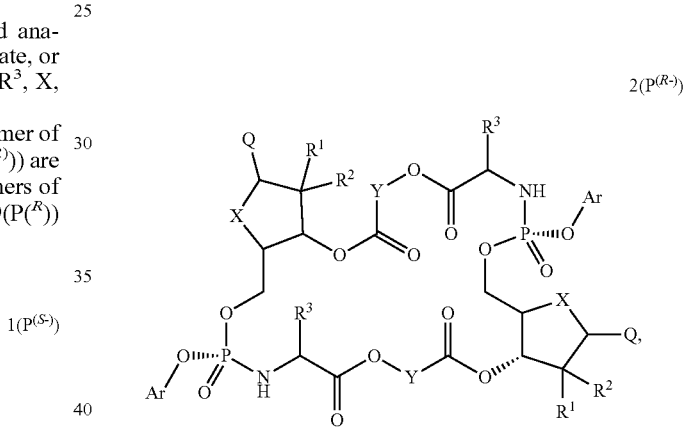

wherein: $1(P^{(S-)})$, $2(P^{(S-)})$, $1(P^{(R-)})$, $2(P^{(R-)})$, and a stereoisomer, isotope-enriched analogue, pharmaceutically acceptable salt, hydrate, solvate, or crystalline or polymorphic form thereof; Ar, $R^1$, $R^2$, $R^3$, X, Y, and Q are as defined above.

The acids $19(P^{(S)})$, $19(P^{(R)})$ are prepared by reaction of chlorides 8 with pentafluorophenol (Scheme 4). The resulting reaction phosphoric enantiomeric mixtures 17 is separated into individual phosphoric enantiomers $17(P^{(S)})$ and $17(P^{(R)})$ by crystallization from a suitable solvent or by chromatography. Reaction of the last compounds with the nucleosides 12 gives compounds $18(P^{(S)})$, $18(P^{(R)})$, which is hydrogenated catalytically to give acids $19(P^{(S)})$, $19(P^{(R)})$.

Scheme 4

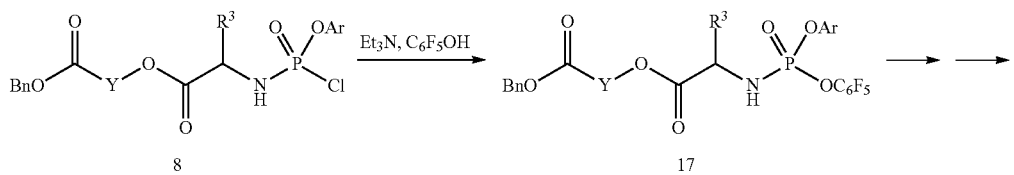

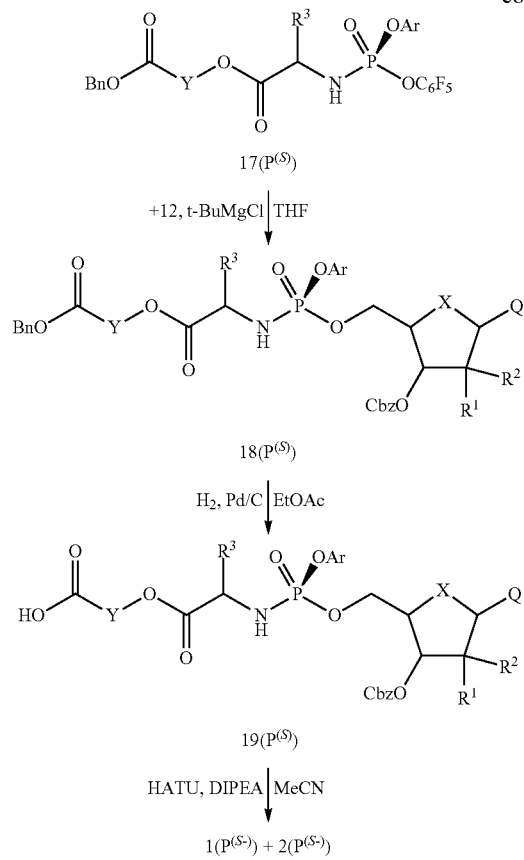

17(P$^{(S)}$)

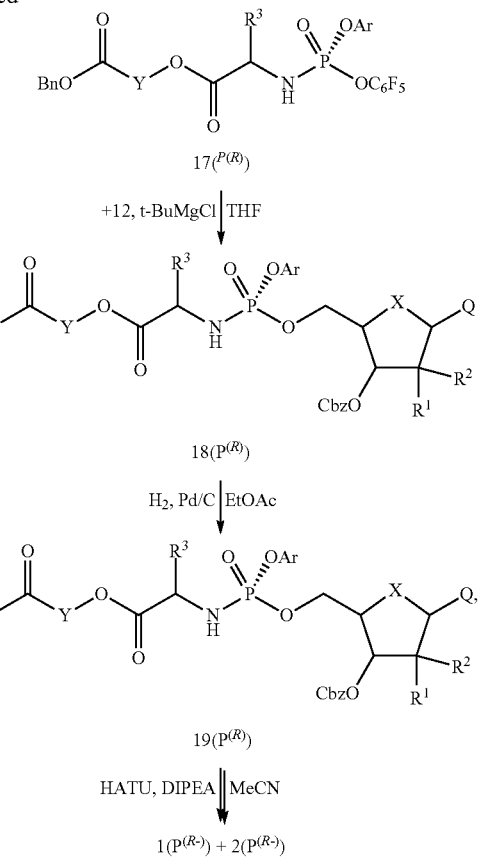

17(P$^{(R)}$)

18(P$^{(S)}$)   18(P$^{(R)}$)

19(P$^{(S)}$)   19(P$^{(R)}$)

1(P$^{(S\text{-})}$) + 2(P$^{(S\text{-})}$)   1(P$^{(R\text{-})}$) + 2(P$^{(R\text{-})}$)

wherein: 1(P$^{(S\text{-})}$), 2(P$^{(S\text{-})}$), 1(P$^{(R\text{-})}$), and 2(P$^{(R\text{-})}$), 8, 17, 17(P$^{(S\text{-})}$), 17(P$^{(R)}$), 18(P$^{(S\text{-})}$), 18(P$^{(R)}$), 19(P$^{(S\text{-})}$), 19(P$^{(R)}$), and a stereoisomer, isotope-enriched analogue, pharmaceutically acceptable salt, hydrate, solvate, or crystalline or polymorphic form thereof; Ar, R$^1$, R$^2$, R$^3$, X, Y, and Q are as defined above.

The present disclosure will now be described in connection with certain embodiments, which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

EXAMPLES

Example 1. General Procedure for Preparing Tert-Butoxycarbonylamino)-Propanoates 6a-g

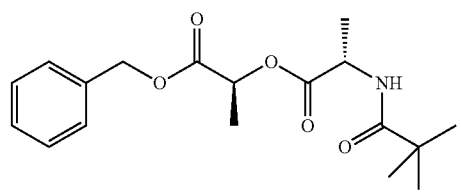

6a

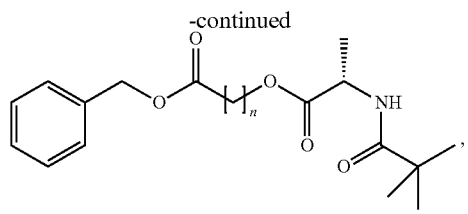

6: n = 2 (b), 3 (c), 4 (d), 5 (e), 6 (f), 7 (g)

To a solution 2.606 g (14.5 mmol) of benzyl L-lactate (4) and 2.764 g (14.6 mmol) of N-Boc-1-alanine (5a) in 100 ml of DCM at 0° C. were added DMAP (0.353 g, 2.9 mmol) and DCC (3.044 g, 14.7 mmol). The reaction was stirred for 15 h at rt and filtered. The precipitate was washed with ether, the combined filtrate was rotovapped and purified by column chromatography on silica gel (hexane: EtOAc 4:1) to give 4.7 g (92%) of 5)-((S)-1-(benzyloxy)-1-oxopropan-2-yl) 2-(tert-butoxycarbonylamino)propanoate (6a) as a viscous colorless oil. 1H NMR (DMSO-d$_6$, 400 MHz) δ: 7.36 (m, 6H), 5.15 (s, 2H), 5.12 (m, 1H), 4.04 (m, 1H), 1.43 (d, J=7.2 Hz, 3H), 1.37 (s, 9H), 1.23 (t, J=7.2 Hz, 3H).

Similarly prepared were: (S)-3-(benzyloxy)-3-oxopropyl 2-(tert-butoxycarbonylamino)propanoate (6b)—yield 97%, $^1$H NMR (DMSO-d$_6$, 400 MHz) δ: 7.36 (m, 5H), 7.24 (d, J=7.6 Hz, 1H), 5.12 (s, 2H), 4.32 (p, J=6.0 Hz, 1H), 4.22 (p, J=6.0 Hz, 1H), 3.95 (p, J=7.2 Hz, 0.9H), 3.87 (m, 0.1H), 2.73 (t, J=6.0 Hz, 2H), 1.37 (s, 8H), 1.32 (brs, 1H), 1.17 (d, J=7.2 Hz, 3H); (S)-benzyl 4-(2-(tert-butoxycarbonylamino) propanoyloxy)butanoate (3c)—yield 96%, $^1$H NMR (DMSO-d$_6$, 400 MHz) δ: 7.36 (m, 5H), 7.26 (d, J=7.6 Hz, 1H), 5.09 (s, 2H), 4.06 (m, 2H), 3.97 (m, 1H), 2.45 (t, J=7.6 Hz, 2H), 1.84 (p, J=6.8 Hz, 2H), 1.36 (s, 8H), 1.31 (brs, 1H), 1.22 (d, J=7.2 Hz, 3H); (S)-benzyl 5-(2-(tert-butoxycarbonylamino)propanoyloxy)pentanoate (3d)—yield 99%, $^1$H NMR (DMSO-d$_6$, 400 MHz) δ 7.36 (m, 5H), 7.23 (d, J=7.2 Hz, 1H), 5.08 (s, 2H), 4.01 (m, 3H), 2.39 (m, 2H), 1.59 (m, 4H), 1.37 (s, 8H), 1.32 (brs, 1H), 1.22 (d, J=7.2 Hz, 3H); (S)-benzyl 6-(2-(tert-butoxycarbonylamino)propanoyloxy)hexanoate (3e)—yield 99%, $^1$H NMR (CDCl$_3$, 400 MHz) δ: 7.37 (m, 5H), 5.13 (s, 2H), 5.05 (brs, 1H), 4.30 (m, 1H), 4.13 (m, 2H), 2.39 (t, J=7.2 Hz, 2H), 1.68 (m, 4H), 1.46 (s, 8.4H), 1.44 (brs, 0.6H), 1.40 (m, 2H), 1.38 (d, J=7.2 Hz, 3H); (5)-benzyl 7-(2-(tert-butoxycarbonylamino)propanoyloxy)heptanoate (3f)—yield 99%, $^1$H NMR (DMSO-d$_6$, 400 MHz) δ: 7.35 (m, 5H), 7.23 (d, J=7.6 Hz, 1H), 5.08 (s, 2H), 4.00 (m, 3H), 2.34 (t, J=7.2 Hz, 2H), 1.54 (m, 4H), 1.37 (s, 8H), 1.33 (brs, 1H), 1.28 (m, 4H), 1.22 (d, J=7.2 Hz, 3H). (S)-benzyl 8-(2-(tert.-butoxycarbonylamino)propanoyloxy)octanoate (3 g)—yield 99%, $^1$H NMR (DMSO-d$_6$, 400 MHz) δ: 7.36 (m, 5H), 7.23 (d, J=7.2 Hz, 1H), 5.08 (s, 2H), 4.00 (m, 3H), 2.34 (t, J=7.2 Hz, 2H), 1.53 (m, 4H), 1.37 (s, 8H), 1.33 (brs, 1H), 1.26 (m, 6H), 1.22 (d, J=7.2 Hz, 3H).

Example 2. General Procedure for Preparing 2-aminopropanoate Hydrochlorides 7a-g

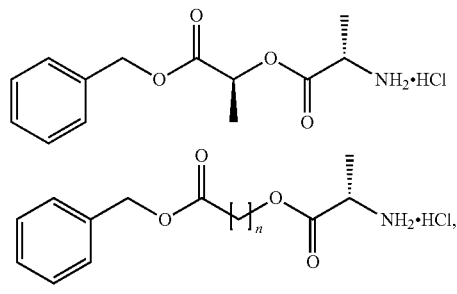

7: n = 2 (b), 3 (c), 4 (d), 5 (e), 6 (f), 7 (g)

To a solution 4.7 g (13.4 mmol) of (5)-((S)-1-(benzyloxy)-1-oxopropan-2-yl) 2-(tert-butoxycarbonylamino)propanoate (6a) in 40 ml of dioxane 40 ml of 3N HCl in dioxane was added. The solution was stirred for 15 h at rt and rotovapped to afford (S)—((S)-1-(benzyloxy)-1-oxopropan-2-yl) 2-aminopropanoate hydrochloride (7a) quantitatively as a viscous colorless oil which slowly crystallized. LC-MS (ESI) 252 (M+H)$^+$, $^1$H NMR (DMSO-d$_6$, 400 MHz) δ: 8.63 (brs, 3H), 7.38 (m, 5H), 5.26 (q, J=7.2 Hz, 1H), 5.19 (m, 2H), 4.15 (q, J=7.2 Hz, 1H), 1.48 (d, J=7.2 Hz, 3H), 1.42 (d, J=7.2 Hz, 3H).

Similarly prepared were: (S)-3-(benzyloxy)-3-oxopropyl 2-aminopropanoate hydrochloride (7b)—LC-MS (ESI) 252 (M+H)$^+$, $^1$H NMR (DMSO-d$_6$, 400 MHz) δ: 8.56 (brs, 3H), 7.37 (m, 5H), 5.13 (s, 2H), 4.43 (m, 1H), 4.33 (m, 1H), 4.01 (m, 1H), 2.80 (t, J=6.0 Hz, 2H), 1.34 (d, J=7.2 Hz, 3H); (S)-benzyl (2-aminopropanoyloxy)butanoate hydrochloride (7c)—LC-MS (ESI) 266(M+H)$^+$; (S)-benzyl 5-(2-aminopropanoyloxy)pentanoate hydrochloride (7d)—LC-MS (ESI) 280 (M+H)$^+$, $^1$H NMR (DMSO-d$_6$, 400 MHz) δ: 8.60 (brs, 3H), 7.36 (m, 5H), 5.09 (s, 2H), 4.15 (m, 2H), 4.04 (m, 1H), 2.41 (m, 2H), 1.63 (m, 4H), 1.41 (d, J=7.2 Hz, 3H); (S)-benzyl 6-(2-aminopropanoyloxy)hexanoate hydrochloride (7e)—LC-MS (ESI) 294 (M+H)$^+$; (S)-benzyl 7-(2-aminopropanoyloxy)heptanoate hydrochloride (7f)—LC-MS (ESI) 308(M+H)$^+$, $^1$H NMR (D$_2$O, 400 MHz) δ: 7.27 (m, 5H), 5.00 (s, 2H), 4.11 (m, 3H), 2.25 (t, J=7.2 Hz, 2H), 1.51 (m, 4H), 1.48 (d, J=7.6 Hz, 3H), 1.19 (m, 4H); (S)-benzyl 8-(2-aminopropanoyloxy)octanoate hydrochloride (7 g)—LC-MS (ESI) 322 (M+H)$^+$, $^1$H NMR (DMSO-d$_6$, 400 MHz) δ: 8.54 (brs, 3H), 7.36 (m, 5H), 5.08 (s, 2H), 4.14 (m, 2H), 4.05 (m, 1H), 2.35 (t, J=7.2 Hz, 2H), 1.56 (m, 4H), 1.41 (d, J=7.2 Hz, 3H), 1.28 (m, 6H).

Example 3. General Procedure for Preparing 2-chloro(phenoxy)phosphorylamino)-propanoates 8a-g

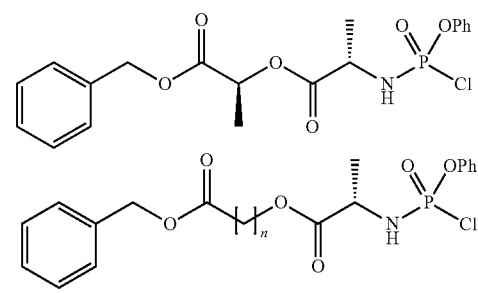

8: n = 2 (b), 3 (c), 4 (d), 5 (e), 6 (f), 7 (g)

A solution 3.035 g (10.5 mmol) of (S)—((S)-1-(benzyloxy)-1-oxopropan-2-yl) 2-aminopropanoate hydrochloride (7a) and phenyl dichlorophosphate (1.575 ml, 10.5 mmol) were dissolved in 40 ml of DCM and cooled to −78° C. A solution of triethylamine (2.86 mL, 21 mmol) in 10 mL of DCM was added dropwise and the resulted mixture was stirred at −78° C. for 1 h and then allowed to warm up to rt. The mixture was rotovapped and the residue was treated with benzene. The precipitate was filtered off and the filtrate was subjected to dry flash chromatography on dry silica gel (washed with MeCN, EtOAc, toluene, hexane) eluting with hexane: EtOAc 2:1 to give 3.8 g (85%) of S)—((S)-1-(benzyloxy)-1-oxopropan-2-yl) 2-(chloro(phenoxy)phosphorylamino)propanoate (8a) as a colourless oil. $^1$H NMR (CDCl$_3$, 400 MHz) δ 7.37 (m, 7H), 7.27 (m, 3H), 5.24 (m, 1H), 5.19 (m, 2H), 4.25 (m, 2H), 1.55 (m, 6H).

Similarly prepared were: (2S)-3-(benzyloxy)-3-oxopropyl 2-(chloro(phenoxy)phosphorylamino)-propanoate (8b)—yield 65%, $^1$H NMR (CDCl$_3$, 400 MHz) δ: 7.37 (m, 7H), 7.26 (m, 3H), 5.16, 5.17 (2s, 2H), 4.49 (m, 2H), 4.20 (m, 2H), 2.75 (q, J=5.6 Hz, 2H), 1.45, 1.46 (2d, J=7.2 Hz, 3H); benzyl 4-((S)-2-(chloro(phenoxy)phosphorylamino)propanoyloxy)butanoate (8c)—yield 49%, $^1$H NMR (CDCl$_3$, 400 MHz) δ: 7.37 (m, 7H), 7.27 (m, 3H), 5.15 (2s, 2H), 4.32 (m, 1H), 4.24 (q, J=6.4 Hz, 2H), 4.18 (m, 1H), 2.48 (m, 2H), 2.05 (m, 2H), 1.51 (2d, J=7.2 Hz, 3H); benzyl 5-((S)-2-(chloro(phenoxy)phosphorylamino)propanoyloxy)pentanoate (8d)—yield 61%, $^1$H NMR (CDCl$_3$, 400 MHz) δ: 7.37 (m, 7H), 7.27 (m, 3H), 5.14 (2s, 2H), 4.34 (m, 1H), 4.20 (m, 2H), 4.16 (m, 1H), 2.42 (m, 2H), 1.74 (m, 4H), 1.51, 1.52 (2d, J=7.2 Hz, 3H); benzyl 6-((S)-2-(chloro (phenoxy)phosphorylamino)propanoyloxy)hexanoate (8e)—yield 22%, $^1$H NMR (CDCl$_3$, 400 MHz) δ: 7.37 (m, 7H), 7.28 (m, 3H), 5.13 (2s, 2H), 4.31 (m, 1H), 4.21 (m, 2H), 4.18 (q, J=6.8 Hz, 2H), 2.38 (m, 2H), 1.70 (m, 4H), 1.51, 1.52 (2d, J=7.2 Hz, 3H), 1.42 (m, 2H); benzyl 74(5)-2-(chloro(phenoxy)phosphorylamino)propanoyloxy)heptanoate (8f)—yield 75%, $^1$H NMR (CDCl$_3$, 400 MHz) δ: 7.37 (m, 7H), 7.27 (m, 3H), 5.13 (s, 2H), 4.33 (m, 1H), 4.17 (m, 3H), 2.37, 2.38 (2t, J=7.4 Hz, 2H), 1.67 (m, 4H), 1.52, 1.53 (2d, J=7.2 Hz, 3H), 1.37 (m, 4H); benzyl 8-((S)-2-(chloro(phenoxy)phosphorylamino)propanoyloxy)octanoate (8 g)—yield 72%; $^1$H NMR (CDCl$_3$, 400 MHz) δ: 7.37 (m, 7H), 7.27 (m, 3H), 5.13 (s, 2H), 4.31 (m, 1H), 4.19 (m, 3H), 2.36, 2.37 (2t, J=7.4 Hz, 2H), 1.65 (m, 4H), 1.52, 1.53 (2d, J=7.2 Hz, 3H), 1.34 (m, 6H).

Example 4. General Procedure for Preparing 1-((2R, 3R, 4R, 5R)-5-((tert-butyldimethylsilyloxy)methyl)-4-hydroxy-tetrahydrofuran-2-yl)pyrimidine-2,4(1H,3H)-diones (10a,b)

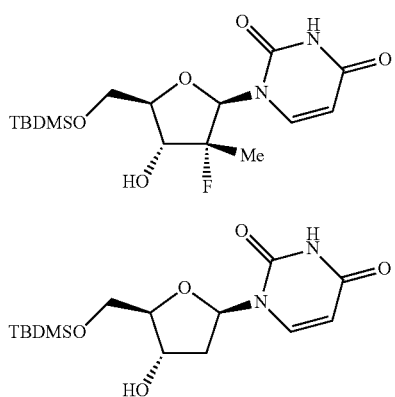

To a solution 1.3 g (5 mmol) of 1-((2R,3R,4R,5R)-3-fluoro-4-hydroxy-5-(hydroxymethyl)-3-methyl-tetrahydrofuran-2-yl)pyrimidine-2,4(1H,3H)-dione (9a) in 10 mL of pyridine was added tert-butylchlorodimethylsilane (866 mg, 5.75 mmol) at 0-5° C. followed by an addition of 1-methylimidazole (0.399 mL, 5 mmol). The mixture was stirred for 3 h, then 3 mL of methanol was added and stirred for 1 h more. The mixture was rotovapped, dissolved in DCM, washed with 5% citric acid solution, with brine, dried over Na$_2$SO$_4$ and rotovapped to afford 1-((2R,3R,4R,5R)-5-((tert-butyldimethylsilyloxy)methyl)-3-fluoro-4-hydroxy-3-methyl-tetrahydrofuran-2-yl)pyrimidine-2,4(1H,3H)-dione (10a) with quantitative yield. LC-MS (ESI) 375 (M+H)$^+$, $^1$H NMR (DMSO-d$_6$, 400 MHz) δ: 11.51 (s, 1H), 7.82 (d, J=8.0 Hz, 1H), 6.00 (d, J=18.8 Hz, 1H), 5.73 (d, J=6.8 Hz, 1H), 5.54 (dd, J$_1$=8.0 Hz, J$_2$=2.4 Hz, 1H), 4.02 (dd, J$_1$=12.0 Hz, J$_2$=1.2 Hz, 1H), 3.89 (m, 1H), 3.80 (m, 2H), 1.27 (d, J=22.4 Hz, 3H), 0.90 (s, 9H), 0.10 (d, J=2.4 Hz, 6H).

Similarly prepared were: 1-((2R, 4S, 5R)-5-((tert-butyldimethylsilyloxy)methyl)-4-hydroxy-tetrahydrofuran-2-yl)pyrimidine-2,4(1H,3H)-dione (10b). From 2'-deoxyuridine. LC-MS (ESI) 343 (M+H)$^+$. $^1$H NMR (DMSO-d$_6$, 400 MHz) δ 11.31 (s, 1H), 7.75 (d, J=8.0 Hz, 1H), 6.14 (t, J=6.8 Hz, 1H), 5.57 (dd, J$_1$=8.0 Hz, J$_2$=2.0 Hz, 1H), 5.29 (d, J=4.4 Hz, 1H), 4.20 (m, 1H), 3.77 (m, 3H), 2.15 (m, 1H), 2.05 (m, 1H), 0.87 (s, 9H), 0.07 (s, 6H).

Example 5. General Procedure for Preparing Benzyl (2R, 3R, 4R, 5R)-2-((tert-butyldimethylsilyloxy)methyl)-5-(2,4-dioxo-3,4-dihydropyrimidin-1(2H)-yl)-tetrahydrofuran-3-yl carbonates (11a,b)

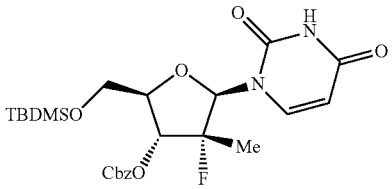

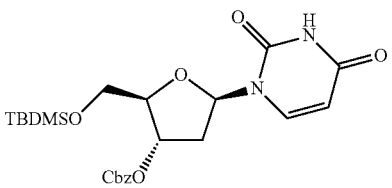

To a solution 1.935 g (5.17 mmol) of 1-((2R,3R,4R,5R)-5-((tert-butyldimethylsilyloxy)methyl)-3-fluoro-4-hydroxy-3-methyl-tetrahydrofuran-2-yl)pyrimidine-2,4(1H,3H)-dione (10a) and DMAP (1.263 g, 10.34 mmol) in 50 mL of DCM was added dropwise benzyl chloroformate (1.107 mL, 7.75 mmol) at 0-5° C. Then the reaction mixture was warmed to room temperature and stirred overnight, then washed with 5% citric acid solution and brine. After drying over Na$_2$SO$_4$ and rotovapping benzyl (2R,3R,4R,5R)-2-((tert-butyldimethylsilyloxy)methyl)-5-(2,4-dioxo-3,4-dihydropyrimidin-1(2H)-yl)-4-fluoro-4-methyl-tetrahydrofuran-3-yl carbonate (11a) was used for the next step without additional purification. Yield quantitative. LC-MS (ESI) 509 (M+H)$^+$. $^1$H NMR (DMSO-d$_6$, 400 MHz) δ: 11.56 (s, 1H), 7.82 (d, J=8.0 Hz, 1H), 7.39 (m, 5H), 6.04 (d, J=18.8 Hz, 1H), 5.62 (d, J=8.0 Hz, 1H), 5.21 (s, 2H), 5.14 (m, 1H), 4.18 (d, J=9.2 Hz, 1H), 4.18 (dd, J$_1$=12.0 Hz, J$_2$=2.4 Hz, 1H), 3.77 (dd, J$_1$=12.0 Hz, J$_2$=3.2 Hz, 1H), 1.33 (d, J=22.8 Hz, 3H), 0.86 (s, 9H), 0.08 (d, J=3.2 Hz, 6H).

Similarly prepared were benzyl (2R,3S,5R)-2-((tert-butyldimethylsilyloxy)methyl)-5-(2,4-dioxo-3,4-dihydropyrimidin-1(2H)-yl)-tetrahydrofuran-3-yl carbonate (11b)—LC-MS (ESI) 477 (M+H)$^+$, $^1$H NMR (DMSO-d$_6$, 400 MHz) δ: 11.37 (s, 1H), 7.72 (d, J=8.0 Hz, 1H), 7.39 (m, 5H), 6.13 (dd, J$_1$=8.0 Hz, J$_2$=6.0 Hz, 1H), 5.63 (dd, J$_1$=8.0 Hz, J$_2$=2.0 Hz, 1H), 5.17 (s, 2H), 5.14 (m, 1H), 4.14 (m, 1H), 3.80 (m, 2H), 2.43 (m, 1H), 2.27 (m, 1H), 0.87 (s, 9H), 0.07 (s, 6H).

Example 6. General Procedure for Preparing Benzyl (2R, 3R, 4R, 5R)-5-(2,4-dioxo-3,4-dihydropyrimidin-1(2H)-yl)-2-(hydroxymethyl)-tetrahydrofuran-3-yl carbonates (12a,b)

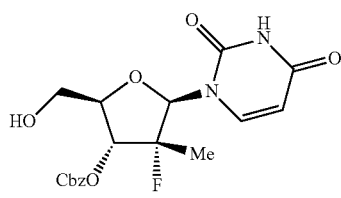

-continued

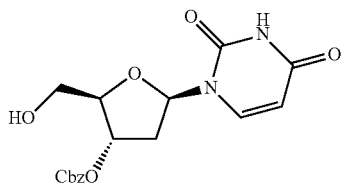
12b

To a solution 2.62 g (5.15 mmol) of benzyl (2R,3R,4R,5R)-2-((tert-butyldimethylsilyloxy)methyl)-5-(2,4-dioxo-3,4-dihydropyrimidin-1(2H)-yl)-4-fluoro-4-methyl-tetrahydrofuran-3-yl carbonate (11a) in 50 mL of DCM was added Et$_3$N.3HF (4.21 mL, 25.75 mmol) and the mixture was stirred for 24 h. The mixture was washed with water, dried over Na$_2$SO$_4$, diluted with 50 ml of toluene and rotovapped to a volume of about 30 mL. The precipitated product was filtered off, washed with hexane and dried. Yield of benzyl (2R,3R,4R,5R)-5-(2,4-dioxo-3,4-dihydropyrimidin-1(2H)-yl)-4-fluoro-2-(hydroxymethyl)-4-methyl-tetrahydrofuran-3-yl carbonate (12a) is 1.715 g (84%). LC-MS (ESI) 395 (M+H)$^+$. $^1$H NMR (DMSO-d$_6$, 400 MHz) δ: 11.53 (s, 1H), 7.94 (d, J=8.0 Hz, 1H), 7.40 (m, 5H), 6.05 (d, J=19.2 Hz, 1H), 5.72 (d, J=8.0 Hz, 1H), 5.36 (brs, 1H), 5.22 (m, 2H), 5.12 (dd, J$_1$=20.0 Hz, J$_2$=8.4 Hz, 1H), 4.12 (m, 1H), 3.80 (m, 1H), 3.61 (m, 1H), 1.33 (d, J=23.2 Hz, 3H).

Similarly prepared were benzyl (2R, 3S, 5R)-5-(2,4-dioxo-3,4-dihydropyrimidin-1(2H)-yl)-2-(hydroxymethyl)-tetrahydrofuran-3-yl carbonate (12b). Yield 80%. LC-MS (ESI) 363 (M+H)$^+$. $^1$H NMR (DMSO-d$_6$, 400 MHz) δ 11.34 (s, 1H), 7.86 (d, J=8.0 Hz, 1H), 7.39 (m, 5H), 6.15 (dd, J$_1$=8.8 Hz, J$_2$=6.0 Hz, 1H), 5.67 (dd, J$_1$=8.0 Hz, J$_2$=2.0 Hz, 1H), 5.19 (m, 2H), 5.17 (s, 2H), 4.07 (m, 1H), 3.62 (m, 2H), 2.37 (m, 1H), 2.29 (m, 1H).

Example 7. General Procedure for Preparing (S)—((S)-1-(benzyloxy)-1-oxopropan-2-yl) 2-((((2R,3R,4R,5R)-3-(benzyloxycarbonyloxy)-5-(2,4-dioxo-3,4-dihydropyrimidin-1(2H)-yl)-tetrahydrofuran-2-yl) methoxy)(phenoxy)phosphorylamino)propanoates (13a-i)

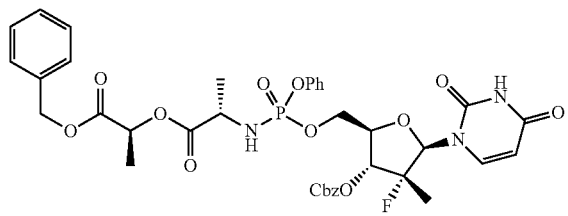
13a

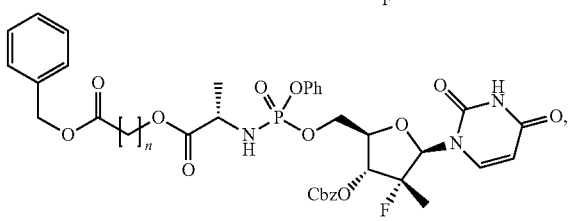

13: n = 2 (b), 3 (c), 4 (d), 5 (e), 6 (f), 7 (g)

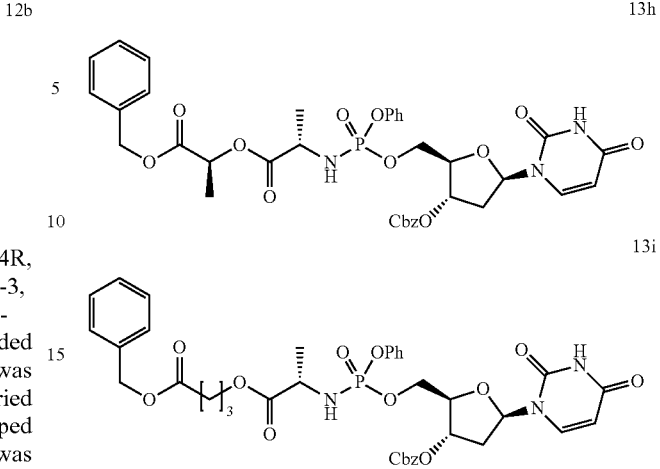
13h

13i

To a solution 197 mg (0.5 mmol) of benzyl (2R,3R,4R,5R)-5-(2,4-dioxo-3,4-dihydropyrimidin-1(2H)-yl)-4-fluoro-2-(hydroxymethyl)-4-methyl-tetrahydrofuran-3-yl carbonate (8a) and 330 mg (0.75 mmol) (S)—((S)-1-(benzyloxy)-1-oxopropan-2-yl) 2-(chloro(phenoxy)phosphorylamino)propanoate (12a) in 10 ml of acetonitrile was added N-methylimidazole (0.159 mL, 1 mmol) and the mixture was stirred for 18 h then quenched with 0.2 mL of methanol. The solvent was rotovapped, the residue was dissolved in DCM, washed with 3% citric acid and brine, dried over Na$_2$SO$_4$, rotovapped subjected to column chromatography on silica gel (hexane: EtOAc 2:3) to give 364 mg (93%) of (S)—((S)-1-(benzyloxy)-1-oxopropan-2-yl) 2-((((2R,3R,4R,5R)-3-(benzyloxycarbonyloxy)-5-(2,4-dioxo-3,4-dihydropyrimidin-1(2H)-yl)-4-fluoro-methyl-tetrahydrofuran-2-yl)methoxy)(phenoxy)phosphorylamino)propanoate (13a) as colourless glassy solid. LC-MS (ESI) 784 (M+H)$^+$.

Similarly prepared were: (S)-3-(benzyloxy)-3-oxopropyl 2-((((2R,3R,4R,5R)-3-(benzyloxycarbonyloxy)-5-(2,4-dioxo-3,4-dihydropyrimidin-1(2H)-yl)-4-fluoro-4-methyl-tetrahydrofuran-2-yl)methoxy)(phenoxy)phosphorylamino) propanoate (13b)—yield 88%, LC-MS (ESI) 784 (M+H)$^+$; benzyl 445)-2-((((2R,3R,4R,5R)-3-(benzyloxycarbonyloxy)-5-(2,4-dioxo-3,4-dihydropyrimidin-1(2H)-yl)-4-fluoro-4-methyl-tetrahydrofuran-2-yl)methoxy)(phenoxy)phosphorylamino)propanoyloxy)butanoate (13c)—yield 81%, LC-MS (ESI) 798 (M+H)$^+$; benzyl 5-((S)-2-((((2R,3R,4R,5R)-3-(benzyloxycarbonyloxy)-5-(2,4-dioxo-3,4-dihydropyrimidin-1(2H)-yl)-4-fluoro-4-methyl-tetrahydrofuran-2-yl)methoxy)(phenoxy)phosphorylamino) propanoyloxy)pentanoate (13d)—yield 84%, LC-MS (ESI) 812 (M+H)$^+$; benzyl 6-((S)-2-((((2R,3R,4R,5R)-3-(benzyloxycarbonyloxy)-5-(2,4-dioxo-3,4-dihydropyrimidin-1 (2H)-yl)-4-fluoro-4-methyl-tetrahydrofuran-2-yl)methoxy) (phenoxy) phosphorylamino)propanoyloxy)hexanoate (9e)—yield 85%, LC-MS (ESI) 826 (M+H)$^+$; benzyl 7-((S)-2-((((2R,3R,4R,5R)-3-(benzyloxycarbonyloxy)-5-(2,4-dioxo-3,4-dihydropyrimidin-1(2H)-yl)-4-fluoro-4-methyl-tetrahydrofuran-2-yl)methoxy)(phenoxy)phosphorylamino) propanoyloxy)heptanoate (9f)—yield 80%, LC-MS (ESI) 840 (M+H)$^+$, $^1$H NMR (DMSO-d$_6$, 400 MHz) δ: 11.57 (s, 1H), 7.66 (d, J=8.0 Hz, 1H), 7.36 (m, 12H), 7.18 (m, 3H), 6.07 (m, 2H), 5.63 (t, J=8.6 Hz, 1H), 5.20 (m, 3H), 5.07 (s, 2H), 4.31 (m, 3H), 3.97 (m, 2H), 3.84 (m, 1H), 2.31, 2.32 (2t, J=7.2 Hz, 2H), 1.49 (m, 4H), 1.34 (d, J=22.8 Hz, 3H), 1.23 (m, 7H); benzyl 8-((S)-2-(4(2R,3R,4R,5R)-3-(benzyloxycarbonyloxy)-5-(2,4-dioxo-3,4-dihydropyrimidin-1(2H)-yl)-4-fluoro-4-methyl-tetrahydrofuran-2-yl)methoxy)(phenoxy)-phosphorylamino)propanoyloxy)octanoate (13 g)—yield 83%, LC-MS (ESI) 854 (M+H)$^+$; (S)—((S)-1-(benzyloxy)-1-oxopropan-2-yl) 2-(((2R,3S,5R)-3-(benzyloxycarbonyloxy)-5-(2,4-dioxo-3,4-dihydropyrimidin-1(2H)-yl)-tetrahydrofuran-2-yl)methoxy)(phenoxy)phosphorylamino)propanoate (13 h)—yield 70%, LC-MS (ESI) 752 (M+H)$^+$, $^1$H NMR (400 MHz, DMSO-d$_6$) δ: 11.38 (s, 1H), 7.59, 7.62 (2d, J=8.4 Hz, 1H), 7.37 (m, 12H), 7.19 (m, 3H), 6.15 (m, 2H), 5.57 (m, 1H), 5.18 (m, 1H), 5.17 (s, 2H), 5.15 (s, 2H), 5.07 (m, 1H), 4.24 (m, 3H), 3.94 (m, 1H), 2.36 (m, 1H), 2.23 (m, 1H), 1.40, 1.41 (2d, J=6.8 Hz, 3H), 1.23, 1.25 (2d, J=7.2 Hz, 3H); benzyl 4((S)-2-((((2R,3S,5R)-3-(benzyloxycarbonyloxy)-5-(2,4-dioxo-3,4-dihydropyrimidin-1(2H)-yl)tetrahydrofuran-2-yl)methoxy)(phenoxy)phosphorylamino) propanoyloxy)butanoate (13i)—yield 81%, LC-MS (ESI) 766 (M+H)$^+$, $^1$H NMR (400 MHz, DMSO-d$_6$) δ: 11.39 (s, 1H), 7.59 (t, J=7.6 Hz, 1H), 7.36 (m, 12H), 7.18 (m, 3H), 6.12 (m, 2H), 5.54, 5.61 (2dd, J$_1$=8.0 Hz, J$_2$=2.0 Hz, 1H), 5.18 (m, 1H), 5.17 (s, 2H), 5.07, 5.08 (2s, 2H), 4.24 (m, 3H), 4.03 (m, 2H), 3.86 (m, 1H), 2.43 (t, J=7.2 Hz, 2H).

Example 8. General Procedure for Preparing S)-2-((S)-2-(4(2R,3R,4R,5R)-5-(2,4-dioxo-3,4-dihydropyrimidin-1(2H)-yl)-3-hydroxy-tetrahydrofuran-2-yl)methoxy)(phenoxy)phosphorylamino)propanoyloxy)propanoic acid (3a-i)

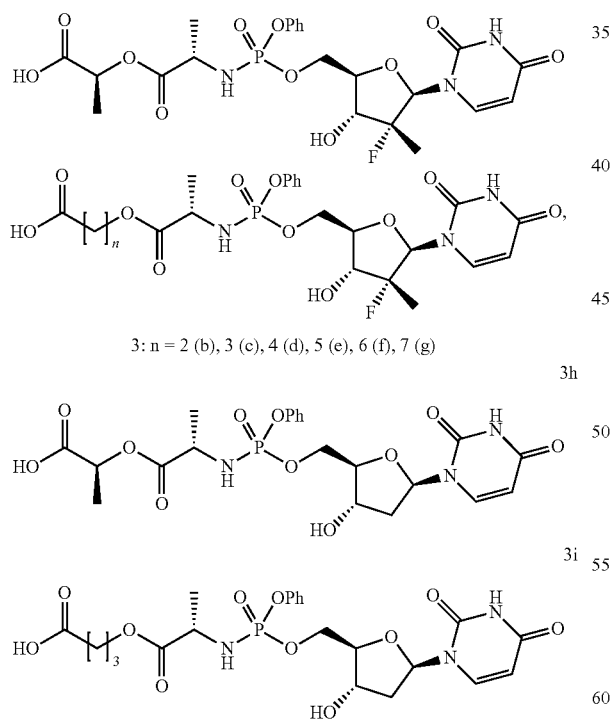

3: n = 2 (b), 3 (c), 4 (d), 5 (e), 6 (f), 7 (g)

A solution 364 mg (0.46 mmol) of compound 13a in 20 ml of EtOAc was stirred with 40 mg of 10% Pd/C under hydrogen for 12 h. The resulted solution was filtered through a celite and rotovapped to afford 260 mg (100%) of S)-2-((S)-2-(4(2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)phosphorylamino)propanoyloxy) propanoic acid (3a). LC-MS (ESI) 560 (M+H)$^+$. $^1$H NMR (DMSO-d$_6$, 400 MHz) δ: 13.00 (brs, 1H), 11.51 (s, 1H), 7.55 (d, J=8.0 Hz, 1H), 7.38 (m, 2H), 7.21 (m, 3H), 6.14 (m, 1H), 6.03 (m, 1H), 5.55 (m, 1H), 4.89 (m, 1H), 4.40 (m, 1H), 4.25 (m, 1H), 4.02 (m, 1H), 3.87 (m, 2H), 1.37, 1.38 (2d, J=7.2 Hz, 3H), 1.26 (m, 6H).

Similarly prepared were: 3-((S)-2-((((2R,3R,4R,5R)-5-(2,4-dioxo-3,4-dihydropyrimidin-1 (2H)-yl)-4-fluoro-3-hydroxy-4-methyl-tetrahydrofuran-2-yl)methoxy)(phenoxy)phosphorylamino)propanoyloxy) propanoic acid (3b)—LC-MS (ESI) 560 (M+H)$^+$; 4-((S)-2-((((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)phosphorylamino)propanoyloxy)butanoic acid (3c)—LC-MS (ESI) 574 (M+H)$^+$; 5-((S)-2-((((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)phosphorylamino)propanoyloxy)pentanoic acid (3d)—LC-MS (ESI) 588 (M+H)$^+$; 6-((S)-2-((((2R,3R,4R,5R)-5-(2,4-dioxo-3,4-dihydropyrimidin-1 (2H)-yl)-4-fluoro-3-hydroxy-4-methyl-tetrahydrofuran-2-yl)methoxy)(phenoxy)phosphorylamino)propanoyloxy)-hexanoic acid (3e)—LC-MS (ESI) 602 (M+H)$^+$; 7-((S)-2-((((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)phosphorylamino) propanoyloxy)heptanoic acid (3f)—LC-MS (ESI) 616 (M+H)$^+$; 7-((S)-2-((((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy) (phenoxy)phosphorylamino)propanoyloxy)-octanoic acid (3 g)—LC-MS (ESI) 630 (M+H)$^+$; (S)-2-((S)-2-((((2R,3S,5R)-3-hydroxy-5-(2,4-Dioxo-3,4-dihydropyrimidin-1(2H)-yl)-tetrahydrofuran-2-yl)methoxy)(phenoxy)phosphorylamino)propanoyloxy)propanoic acid (3H)—LC-MS (ESI) 542 (M+H)$^+$; 4-((S)-2-((((2R,3S,5R)-3-hydroxy-5-(2,4-dioxo-3,4-dihydropyrimidin-1(2H)-yl)tetrahydrofuran-2-yl)methoxy)(phenoxy)phosphorylamino)propanoyloxy)butanoic acid (3i). LC-MS (ESI) 556 (M+H)$^+$.

Example 9. Procedure for Preparing (S)—((S)-1-(benzyloxy)-1-oxopropan-2-yl) 2-((S)-(perfluorophenoxy)(phenoxy)phosphorylamino)propanoate (17a)

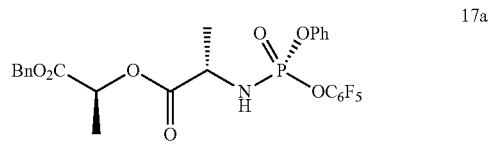

To a solution 6.247 g (14.7 mmol) of (S)—((S)-1-(benzyloxy)-1-oxopropan-2-yl) 2-(chloro(phenoxy)phosphorylamino)propanoate (8a) in 70 mL of anhydrous DCM was added dropwise a solution 2.7 g (14.7 mmol) of pentafluorophenol and triethylamine (1.99 mL, 14.7 mmol) in 20 mL of DCM at 0° C. The mixture was stirred at rt for 15 h and rotovapped. The residue was treated with 150 mL of toluene, the solution was filtered and rotovapped again. The residue was treated with 100 mL of 4:1 hexane/EtOAc. After 1 h the precipitate was filtered, washed with hexane and recrystallized from 100 mL of 4:1 Hexane/EtOAc to afford 2.766 g (33%) of (S)—((S)-1-(benzyloxy)-1-oxopropan-2-yl)

2-((S)-(perfluorophenoxy)(phenoxy)phosphorylamino)propanoate (17a) as a white solid. LC-MS (ESI) 574 (M+H)+, 1H NMR (CDCl3, 400 MHz) δ: 7.36 (m, 7H), 7.25 (m, 3H), 5.19 (m, 3H), 4.27 (m, 1H), 3.89 (m, 1H), 1.54 (d, J=7.2 Hz, 3H), 1.49 (d, J=7.2 Hz, 3H).

Example 10. Procedure for Preparing Benzyl 4-((S)-2-((S)-(perfluorophenoxy)(phenoxy)phosphorylamino)propanoyloxy)butanoate (17b)

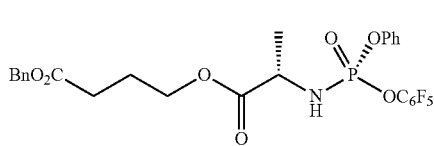

17b

To a solution 5.8 g (13.2 mmol) of benzyl 4-((S)-2-(chloro(phenoxy)phosphorylamino)propanoyloxy)butanoate (8b) in 70 mL of anhydrous DCM was added a solution 2.43 g (13.2 mmol) of pentafluorophenol and triethylamine (1.84 mL, 13.2 mmol) in 10 mL of dichloromethane at 0° C. The mixture was stirred at rt for 15 h and rotovapped. The residue was treated with 150 mL of toluene, the solution was filtered and rotovapped again. The residue was treated with 100 mL of hexane. After 1 h the formed precipitate was filtered, washed with hexane and air-dried. The product was washed with water and air-dried. Benzyl 4-((S)-2-((S)-(perfluorophenoxy)(phenoxy)phosphorylamino)propanoyloxy)butanoate (17b) was obtained as a white solid, 5.8 g, 75%. LC-MS (ESI) 588 (M+H)+. 1H NMR (CDCl3, 400 MHz) δ: 7.36 (m, 7H), 7.24 (m, 3H), 5.14 (s, 2H), 4.19 (m, 3H), 3.97 (m, 1H), 2.45 (t, J=7.2 Hz, 2H), 2.02 (m, 2H), 1.47 (d, J=6.8 Hz, 3H).

Example 11. General Procedure for Preparing Compounds 18aP(S), 18cP(S) and 18iP(S)

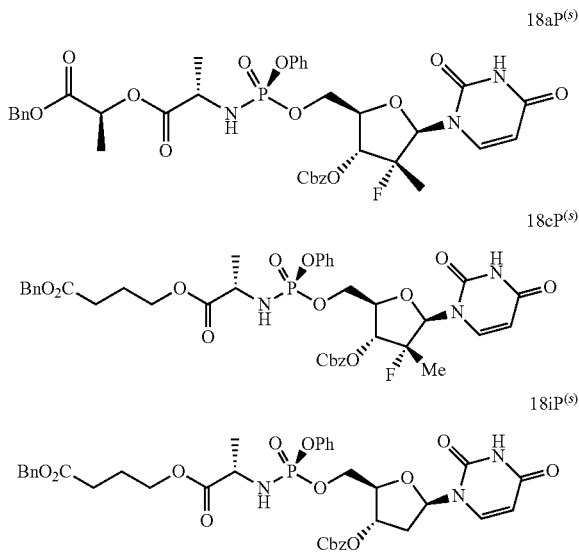

To a solution 789 mg (2 mmol) of benzyl (2R,3R,4R,5R)-5-(2,4-dioxo-3,4-dihydropyrimidin-1(2H)-yl)-4-fluoro-2-(hydroxymethyl)-4-methyl-tetrahydrofuran-3-yl carbonate (12a) in 40 mL of THF under Ar was added tert-butylmagnesium chloride 1M solution in THF (4.2 mL, 4.2 mmol) and the mixture was stirred for 0.5 h at rt. A solution 0.63 g (1.1 mmol) of (S)—((S)-1-(benzyloxy)-1-oxopropan-2-yl) 2-((S)-(perfluorophenoxy)(phenoxy)phosphorylamino)propanoate (17a) in 5 ml of THF was added by syringe and the mixture was stirred overnight under Ar at rt. The reaction mixture was quenched with 1 mL of methanol, rotovapped, the residue was dissolved in DCM, washed with 5% citric acid, saturated NaHCO3, brine, dried over Na2SO4 and rotovapped. The desired product was separated by column chromatography on silica gel (hexane: EtOAc 1:1, 1:2, 0:1). Yield of (S)—((S)-1-(benzyloxy)-1-oxopropan-2-yl) 2-((S)-(((2R,3R,4R,5R)-3-(benzyloxycarbonyloxy)-5-(2,4-dioxo-3,4-dihydropyrimidin-1(2H)-yl)-4-fluoro-4-methyl-tetrahydrofuran-2-yl)methoxy)(phenoxy)phosphorylamino)propanoate (18aP(S)) is 700 mg (44%). LC-MS (ESI) 784 (M+H)+.

Similarly prepared were: benzyl 4-((S)-2-((S)-(((2R,3R,4R,5R)-3-(benzyloxycarbonyloxy)-5-(2,4-dioxo-3,4-dihydropyrimidin-1(2H)-yl)-4-fluoro-4-methyl-tetrahydrofuran-2-yl)methoxy)(phenoxy)phosphorylamino)propanoyloxy)butanoate (18cP(S))—yield 69%, LC-MS (ESI) 798 (M+H)+, 1H NMR (DMSO-d6, 400 MHz) δ: 11.55 (s, 1H), 7.66 (d, J=8.0 Hz, 1H), 7.37 (m, 12H), 7.17 (m, 3H), 6.08 (dd, J1=12.8 Hz, J2=10.4 Hz, 1H), 6.01 (m, 1H), 5.62 (d, J=8.0 Hz, 1H), 5.20 (m, 3H), 5.08 (s, 2H), 4.34 (m, 1H), 4.27 (m, 2H), 4.03 (m, 2H), 3.86 (m, 1H), 2.42 (t, J=7.6 Hz, 2H), 1.82 (p, J=6.8 Hz, 2H), 1.34 (d, J=23.2 Hz, 3H), 1.22 (d, J=7.2 Hz, 3H); benzyl 4-((S)-2-((((2R,3S,5R)-3-(benzyloxycarbonyloxy)-5-(2,4-dioxo-3,4-dihydropyrimidin-1(2H)-yl)-tetrahydrofuran-2-yl)methoxy)(phenoxy)phosphorylamino)propanoyloxy)butanoate (18iP(S))—yield 94%, LC-MS (ESI) 766 (M+H)+.

Example 12. General Procedure for Preparing Compounds 19aP(S), 19cP(S) and 19iP(S)

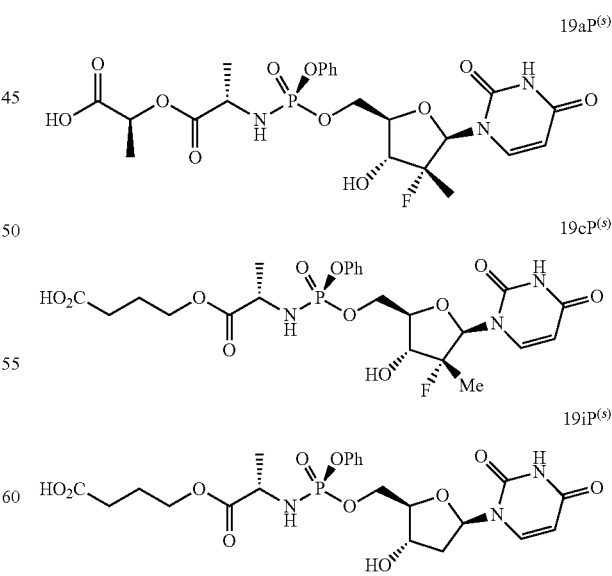

A solution 700 mg (0.9 mmol) of compound 18aP(S) in 25 ml of EtOAc was stirred with 70 mg of 10% Pd/C under hydrogen for 12 h. The resulted solution was filtered through a celite and rotovapped to afford 499 mg (100%) of (S)-2-((S)-2-((S)-(((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)phosphorylamino)propanoyloxy)propanoic acid (19aP$^{(S)}$). LC-MS (ESI) 560 (M+H)$^+$.

Similarly prepared were: 4((S)-2-((S)-(((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)pho sphorylamino) propanoyloxy)butanoic acid (19cP$^{(S)}$)—LC-MS (ESI) 574 (M+H)$^+$, $^1$H NMR (DMSO-d$_6$, 400 MHz) δ: 12.11 (s, 1H), 11.50 (s, 1H), 7.56 (d, J=8.0 Hz, 1H), 7.37 (m, 2H), 7.30 (m, 3H), 6.07 (dd, J$_1$=12.8 Hz, J$_2$=10.4 Hz, 1H), 6.01 (m, 1H), 5.83 (d, J=8.0 Hz, 1H), 5.54 (dd, J$_1$=8.0 Hz, J$_2$=2.0 Hz, 1H), 4.37 (m, 1H), 4.24 (m, 1H), 4.02 (m, 3H), 3.86 (m, 2H), 2.27 (t, J=7.2 Hz, 2H), 1.77 (p, J=6.8 Hz, 2H), 1.25 (d, J=22.4 Hz, 3H), 1.25 (d, J=7.2 Hz, 3H); 4-((S)-2-((((2R,3S,5R)-5-(2,4-dioxo-3,4-dihydropyrimidin-1(2H)-yl)-3-hydroxytetrahydrofuran-2-yl)methoxy)(phenoxy)phosphorylamino)propanoyloxy)butanoic acid (19iP$^{(S)}$)—LC-MS (ESI) 542 (M+H)$^+$.

Example 13. General Procedure for Preparing Macroheterocyclic Nucleoside Derivative and their Analogue of the General Formula (1) or (2)

Cyclization of the acids 10a-i, 19aP$^{(S)}$, 19cP$^{(S)}$, and 19iP$^{(S)}$ (general procedure). To a solution 0.5 mmol of the acid 10a-i, 19aP$^{(S)}$, 19cP$^{(S)}$, or 19iP$^{(S)}$ and HATU (209 mg, 0.55 mmol) in 10 mL of dry MeCN was added DIPEA (0.218 mL, 1.25 mmol) and the mixture was stirred for 24 h. The solution was rotovapped, dissolved in DCM, washed with 5% citric acid solution, with brine, rotovapped and subjected to column chromatography on silica gel (hexane: EtOAc 1:3-1:4). Corresponding macroheterocyclic nucleoside derivative and their analogue of the general formula 1 or 2 is prepared in the form of mixtures or individual enantiomers. Mixtures of enantiomers 1 and 2 were separated by crystallization from a suitable solvent or by chromatography. (2R,3aS,6S,9S,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(1/2)), LC-MS (ESI) 510 (M+H)$^+$. (2R,3aS,6S,9S,11S,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(1)), LC-MS (ESI) 510 (M+H)$^+$, $^1$H NMR (DMSO-d$_6$, 400 MHz) δ 11.33 (s, 1H), 7.72 (d, J=8.0 Hz, 1H), 7.38 (m, 2H), 7.22 (m, 2H), 7.19 (m, 1H), 6.16 (m, 2H), 5.62 (d, J=8.0 Hz, 1H), 5.06 (m, 1H), 4.92 (q, J=7.0 Hz, 1H), 4.26 (m, 1H), 4.16 (m, 2H), 3.88 (m, 1H), 2.62 (m, 1H), 2.36 (m, 1H), 1.47 (d, J=7.2 Hz, 3H), 1.32 (d, J=7.2 Hz, 3H). (2R,3aS,6S,9S,11R,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(2)), LC-MS (ESI) 510 (M+H)$^+$, $^1$H NMR (DMSO-d$_6$, 400 MHz) δ 11.32 (s, 1H), 7.66 (d, J=8.0 Hz, 1H), 7.40 (m, 2H), 7.22 (m, 3H), 6.34 (dd, J$_1$=15.2 Hz, J$_2$=9.6 Hz, 1H), 6.13 (dd, J$_1$=8.0 Hz, J$_2$=2.8 Hz, 1H), 5.59 (d, J=8.0 Hz, 1H), 5.02 (q, J=8.0 Hz, 1H), 4.92 (q, J=6.8 Hz, 1H), 4.44 (m, 1H), 4.05 (m, 1H), 3.91 (m, 1H), 3.75 (m, 1H), 2.66 (m, 1H), 2.37 (m, 1H), 1.47 (d, J=6.8 Hz, 3H), 1.24 (d, J=6.8 Hz, 3H). (2R,3R,3aR,6S,9S,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(3/4)) 542 (M+H)$^+$. (2R,3R,3aR,6S,9S,11S,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(3)), LC-MS (ESI) 542 (M+H)$^+$, $^1$H NMR (DMSO-d$_6$, 400 MHz) δ11.56 (s, 1H), 7.73 (d, J=8.0 Hz, 1H), 7.41 (m, 2H), 7.22 (m, 3H), 6.42 (dd, J$_1$=14.8 Hz, J$_2$=9.2 Hz, 1H), 6.16 (brs, 0.5H), 5.67 (d, J=8.0 Hz, 1H), 5.29 (brs, 0.5H), 4.98 (q, J=6.8 Hz, 1H), 4.44 (m, 1H), 4.24 (m, 2H), 3.78 (m, 1H), 1.52 (d, J=6.8 Hz, 3H), 1.36 (d, J=24.0 Hz, 3H), 1.27 (d, J=6.8 Hz, 3H). (2R,3R,3aR,6S,9S,11R,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(4)), LC-MS (ESI) 542 (M+H)$^+$, $^1$H NMR (DMSO-d$_6$, 400 MHz) δ 11.47 (s, 1H), 7.46 (s, 1H), 7.36 (m, 2H), 7.22 (m, 2H), 7.18 (m, 1H), 6.18 (m, 2H), 6.05 (d, J=4.8 Hz, 1H), 5.11 (m, 0.5H), 4.98 (m, 0.5H), 4.91 (m, 2H), 4.22 (m, 3H), 3.99 (m, 1H), 3.91 (m, 1H), 1.52 (d, J=6.8 Hz, 3H), 1.36 (d, J=24.0 Hz, 3H), 1.27 (d, J=6.8 Hz, 3H). (2R,3R,3aR,10S,14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(5/6)), LC-MS (ESI) 542 (M+H)$^+$. (2R,3R,3aR,10S,12S,14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(5)), LC-MS (ESI) 542 (M+H)$^+$. (2S,3aS,11S,15aR)-2-(2-amino-6-oxo-1,6-dihydro-purin-9-yl)-11-methyl-1-methylene-13-oxo-13-phenoxy-decahydro-4,9,14-trioxa-12-aza-13-phospha-cyclopentacyclotetradecene-5,10-dione (1(7/8)), LC-MS (ESI) 556 (M+H)$^+$.

(2S,3aS,11S,13S,15aR)-2-(2-amino-6-oxo-1,6-dihydro-purin-9-yl)-11-methyl-1-methylene-13-oxo-13-phenoxy-decahydro-4,9,14-trioxa-12-aza-13-phospha-cyclopentacyclotetradecene-5,10-dione (1(7)), LC-MS (ESI) 556 (M+H)$^+$, $^1$H NMR (DMSO-d$_6$, 400 MHz) δ 11.53 (s, 1H), 7.40 (m, 3H), 7.27 (m, 2H), 7.20 (m, 1H), 6.27 (dd, J$_1$=14.8 Hz, J$_2$=11.6 Hz, 1H), 6.08 (d, J=20.0 Hz, 1H), 5.26 (brs, 1H), 5.10 (brs, 1H), 4.40 (m, 2H), 4.29 (m, 1H), 4.20 (m, 2H), 3.65 (m, 1H), 2.57 (m, 2H), 2.05 (m, 1H), 1.96 (m, 1H), 1.29 (d, J=22.8 Hz, 3H), 1.21 (d, J=7.2 Hz, 3H). (2S,3S,3aS,11S,13R,15aR)-2-(6-amino-purin-9-yl)-3,11-dimethyl-1-methylene-13-oxo-13-phenoxy-decahydro-4,9,14-trioxa-12-aza-13-phospha-cyclopentacyclotetradecene-5,10-dione (1(8)), LC-MS (ESI) 556 (M+H)$^+$, $^1$H NMR (DMSO-d$_6$, 400 MHz) δ 11.56 (s, 1H), 7.72 (d, J=8.0 Hz, 1H), 7.39 (m, 2H), 7.21 (m, 3H), 6.17 (t, J=7.2 Hz, 1H), 6.08 (d, J=20.0 Hz, 1H), 5.62 (d, J=8.0 Hz, 1H), 5.40 (m, 1H), 4.35 (m, 3H), 4.20 (m, 2H), 3.80 (m, 1H), 2.62 (m, 2H), 2.07 (m, 1H), 1.90 (m, 1H), 1.30 (d, J=22.8 Hz, 3H), 1.18 (d, J=7.2 Hz, 3H). (2R,3aS,11S,15aR)-2-(2,4-dioxo-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(9/10)), LC-MS (ESI) 524 (M+H)$^+$. (2R,3aS,11S,13S,15aR)-2-(2,4-dioxo-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(9)), LC-MS (ESI) 524 (M+H)$^+$, $^1$H NMR (DMSO-d$_6$, 400 MHz) δ 11.32 (s, 1H), 7.55 (d, J=8.0 Hz, 1H), 7.38 (m, 2H), 7.24 (m, 2H), 7.19 (m, 1H), 6.19 (dd, J$_1$=14.4 Hz, J$_2$=11.2 Hz, 1H), 6.13 (dd, J$_1$=6.8 Hz, J$_2$=6.0 Hz, 1H), 5.43 (d, J=8.0 Hz, 1H), 5.30 (m, 1H), 4.38 (m, 1H), 4.14 (m, 3H), 4.03 (m, 1H), 3.64 (m, 1H), 2.55 (m, 1H), 2.44 (m, 2H), 2.29 (m, 1H), 1.99 (m, 2H), 1.21 (d, J=6.8 Hz, 3H). (2S, 3aR,11S,13R,15aS)-11-methyl-2-(5-methyl-2,4-dioxo-3,4-dihydro-2H-pyrimidin-1-yl)-13-oxo-13-phenoxy-octahydro-1,4,9,14-tetraoxa-12-aza-13-phospha-cyclopentacyclotetradecene-5,10-dione (1(10)), LC-MS (ESI) 524 (M+H)⁺, ¹H NMR (DMSO-d₆, 400 MHz) δ 11.36 (s, 1H), 7.73 (d, J=8.0 Hz, 1H), 7.38 (m, 2H), 7.20 (m, 3H), 6.14 (t, J=6.8 Hz, 1H), 6.05 (t, J=10.8 Hz, 1H), 5.64 (d, J=8.0 Hz, 1H), 5.33 (m, 1H), 4.35 (m, 1H), 4.21 (m, 2H), 4.11 (m, 2H), 3.80 (m, 1H), 2.47 (m, 3H), 2.29 (m, 1H), 2.02 (m, 1H), 1.89 (m, 2H), 1.13 (d, J=6.8 Hz, 3H). (2R,3R,3aR,11S,5aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(13/14)), LC-MS (ESI) 556 (M+H)⁺. (2R, 3R, 3aR, 11S, 13S, 15aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(13)), LC-MS (ESI) 556 (M+H)⁺, ¹H NMR (DMSO-d₆, 400 MHz) δ 11.53 (s, 1H), 7.40 (m, 3H), 7.27 (m, 2H), 7.20 (m, 1H), 6.27 (dd, J₁=14.8 Hz, J₂=11.6 Hz, 1H), 6.08 (d, J=20.0 Hz, 1H), 5.26 (brs, 1H), 5.10 (brs, 1H), 4.40 (m, 2H), 4.29 (m, 1H), 4.20 (m, 2H), 3.65 (m, 1H), 2.57 (m, 2H), 2.05 (m, 1H), 1.96 (m, 1H), 1.29 (d, J=22.8 Hz, 3H), 1.21 (d, J=7.2 Hz, 3H).

(2R,3R,3aR,11S,13R,15aR)-2-(2,4-Dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(14)), LC-MS (ESI) 556 (M+H)⁺. ¹H NMR (DMSO-d₆, 400 MHz) δ 11.56 (s, 1H), 7.72 (d, J=8.0 Hz, 1H), 7.39 (m, 2H), 7.21 (m, 3H), 6.17 (t, J=7.2 Hz, 1H), 6.08 (d, J=20.0 Hz, 1H), 5.62 (d, J=8.0 Hz, 1H), 5.40 (m, 1H), 4.35 (m, 3H), 4.20 (m, 2H), 3.80 (m, 1H), 2.62 (m, 2H), 2.07 (m, 1H), 1.90 (m, 1H), 1.30 (d, J=22.8 Hz, 3H), 1.18 (d, J=7.2 Hz, 3H). (2R,3R,3aR, 12S,16aR)-2-(2,4-Dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(17/18)), LC-MS (ESI) 560 (M+H)⁺. (2R,3R,3aR,12S,14S,16aR)-2-(2,4-Dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(17)), LC-MS (ESI) 560 (M+H)⁺, ¹H NMR (DMSO-d₆, 400 MHz) δ 11.55 (s, 1H), 7.54 (brs, 1H), 7.40 (m, 2H), 7.22 (m, 3H), 6.21 (dd, J₁=14.4 Hz, J₂=10.4 Hz, 1H), 6.05 (brs, 1H), 5.43 (brs, 1H), 5.28 (brs, 1H), 4.48 (m, 1H), 4.39 (m, 1H), 4.17 (m, 2H), 4.09 (m, 1H), 3.80 (m, 1H), 2.58 (m, 1H), 2.42 (m, 1H), 1.83 (m, 1H), 1.72 (m, 1H), 1.65 (m, 2H), 1.29 (d, J=22.8 Hz, 3H), 1.20 (d, J=6.8 Hz, 3H). (2R,3R,3aR,12S,14R,16aR)-2-(2,4-Dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(18)), LC-MS (ESI) 560 (M+H)⁺, ¹H NMR (DMSO-d₆, 400 MHz) δ 11.55 (s, 1H), 7.74 (d, J=8.0 Hz, 1H), 7.38 (m, 2H), 7.19 (m, 3H), 6.11 (brs, 1H), 6.01 (m, 1H), 5.69 (d, J=8.0 Hz, 1H), 5.21 (brs, 1H), 4.43 (m, 1H), 4.28 (m, 2H), 4.09 (m, 2H), 3.86 (m, 1H), 2.66 (m, 1H), 2.30 (m, 1H), 1.85 (m, 1H), 1.69 (m, 2H), 1.51 (m, 1H), 1.32 (d, J=22.8 Hz, 3H), 1.14 (d, J=7.2 Hz, 3H). (2R,3R,3aR,13S,15S,17aR)-2-(2,4-Dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(19/20)), LC-MS (ESI) 584 (M+H)⁺. (2R,3R,3aR,13S,15S,17aR)-2-(2,4-Dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(19)), LC-MS (ESI) 584 (M+H)⁺, ¹H NMR (DMSO-d₆, 400 MHz) δ 11.56 (s, 1H), 7.66 (d, J=8.0 Hz, 1H), 7.37 (m, 2H), 7.19 (m, 3H), 6.05 (m, 2H), 5.58 (d, J=8.0 Hz, 1H), 5.28 (brs, 1H), 4.35 (m, 1H), 4.26 (m, 2H), 4.19 (m, 1H), 4.01 (m, 1H), 3.86 (m, 1H), 2.47 (m, 2H), 1.61 (m, 4H), 1.35 (m, 2H), 1.30 (d, J=22.8 Hz, 3H), 1.11 (d, J=6.8 Hz, 3H). (2R,3R,3aR,13S,15R,17aR)-2-(2,4-Dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(20)), LC-MS (ESI) 584 (M+H)⁺, ¹H NMR (DMSO-d₆, 400 MHz) δ 11.55 (s, 1H), 7.49 (d, J=6.8 Hz, 1H), 7.41 (m, 2H), 7.28 (m, 2H), 7.21 (m, 1H), 6.19 (dd, J₁=15.2 Hz, J₂=10.4 Hz, 1H), 6.08 (d, J=19.6 Hz, 1H), 5.31 (d, J=6.8 Hz, 1H), 5.17 (brs, 1H), 4.50 (m, 1H), 4.38 (m, 2H), 3.95 (m, 2H), 3.82 (m, 1H), 2.48 (m, 2H), 1.61 (m, 4H), 1.27 (d, J=19.2 Hz, 3H), 1.24 (m, 2H), 1.14 (d, J=6.8 Hz, 3H). (2R,3R,3aR,14S,16S,18aR)-2-(2,4-Dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cyclopentacycloheptadecene-5,13-dione (1(21/22)) LC-MS (ESI) 598 (M+H)⁺. (2R,3R,3aR,14S,16S,18aR)-2-(2,4-Dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cyclopentacycloheptadecene-5,13-dione (1(21)), LC-MS (ESI) 598 (M+H)⁺, ¹H NMR (DMSO-d₆, 400 MHz) δ 11.55 (s, 1H), 7.69 (d, J=8.0 Hz, 1H), 7.37 (m, 2H), 7.17 (m, 3H), 6.04 (m, 2H), 5.63 (d, J=8.0 Hz, 1H), 5.31 (brs, 1H), 4.36 (m, 1H), 4.29 (m, 2H), 4.18 (m, 1H), 4.00 (m, 1H), 3.84 (m, 1H), 2.45 (t, J=6.0 Hz, 2H), 1.70 (m, 1H), 1.57 (m, 3H), 1.34 (m, 4H), 1.31 (d, J=22.8 Hz, 3H), 1.17 (d, J=6.8 Hz, 3H). (2R,3R,3aR,14S,16R,18aR)-2-(2,4-Dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cyclopentacycloheptadecene-5,13-dione (1(22)), LC-MS (ESI) 598 (M+H)⁺, ¹H NMR (DMSO-d₆, 400 MHz) δ 11.54 (s, 1H), 7.59 (d, J=7.6 Hz, 1H), 7.39 (m, 2H), 7.24 (m, 2H), 7.19 (m, 1H), 6.16 (dd, J₁=14.4 Hz, J₂=10.0 Hz, 1H), 6.05 (m, 1H), 5.47 (d, J=7.6 Hz, 1H), 5.29 (brs, 1H), 4.39 (m, 1H), 4.33 (m, 1H), 4.19 (m, 1H), 4.13 (m, 1H), 4.01 (m, 1H), 3.78 (m, 1H), 2.47 (m, 2H), 1.68 (m, 1H), 1.62 (m, 3H), 1.34 (m, 4H), 1.28 (d, J=22.8 Hz, 3H), 1.19 (d, J=6.8 Hz, 3H). (2R,3R,3aR,15S,17S,19aR)-2-(2,4-Dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(23/24)), LC-MS (ESI) 612 (M+H)⁺. (2R,3R,3aR,15S,17S,19aR)-2-(2,4-Dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(23)), LC-MS (ESI) 612 (M+H)⁺, ¹H NMR (DMSO-d₆, 400 MHz) δ 11.55 (s, 1H), 7.56 (d, J=8.0 Hz, 1H), 7.36 (m, 2H), 7.19 (m, 3H), 6.05 (m, 2H), 5.48 (d, J=8.0 Hz, 1H), 5.25 (brs, 1H), 4.33 (m, 4H), 3.92 (m, 1H), 3.84 (m, 1H), 2.44 (m, 2H), 1.58 (m, 4H), 1.30 (m, 6H), 1.28 (d, J=22.8 Hz, 3H), 1.19 (d, J=6.8 Hz, 3H). (2R,3R,3aR,15S, 17R,19aR)-2-(2,4-Dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(24)), LC-MS (ESI) 612 (M+H)⁺, ¹H NMR (DMSO-d₆, 400 MHz) δ 11.54 (s, 1H), 7.65 (d, J=8.0 Hz, 1H), 7.38 (m, 2H), 7.21 (m, 3H), 6.10 (dd, J₁=14.4 Hz, J₂=9.6 Hz, 1H), 6.04 (m, 1H), 5.52 (d, J=8.0 Hz, 1H), 5.24 (brs, 1H), 4.32 (m, 4H), 4.23 (m, 2H), 3.96 (m, 1H), 3.80 (m, 1H), 2.44 (m, 2H), 1.59 (m, 4H), 1.31 (m, 6H), 1.28 (d, J=22.8 Hz, 3H), 1.21 (d, J=6.8 Hz, 3H). (2R,3R,3aR,9S,11S,13aR,15R,16R,16aR,22S,24S,26aR)-2,15-Bis(2,4-dioxo-3,4-dihydropyrimidin-1(2H)-yl)-3,16-difluoro-3,9,16,22-tetramethyl-11,24-diphenoxydodecahydro- 2H,13H-difuro[3,2-j:3',2'-v][1,6,9,13,18,21,3,15,2,14]hexaoxadiazadiphosphacyclotetracosine-5,8,18,21(6H,9H,19H,22H)-tetrone 11,24-dioxide (2(1)), LC-MS (ESI) 1055. (2R,3R,3aR,11S,13S,15aR,17R,18R,18aR,26S,28S,30aR)-2,17-bis(2,4-dioxo-3,4-dihydropyrimidin-1(2H)-yl)-3,18-difluoro-3,11,18,26-tetramethyl-13,28-diphenoxyhexadecahydro-2H,15H-difuro[3,2-1:3',2'-z][1,6,11,15,20,25,3,17,2,16]hexaoxadiazadiphosphacyclooctacosine-5,10,20,25(6H,11H,21H,26H)-tetrone 13,28-dioxide (2(2)), LC-MS (ESI) 1111 (M+H)$^+$, $^1$H NMR (DMSO-d$_6$, 400 MHz) δ 11.55 (s, 2H), 7.65 (d, J=8.0 Hz, 2H), 7.38 (m, 4H), 7.22 (m, 4H), 7.19 (m, 2H), 6.15 (dd, J$_1$=14.0 Hz, J$_2$=10.0 Hz, 2H), 6.03 (m, 2H), 5.57 (d, J=8.0 Hz, 2H), 5.28 (brs, 2H), 4.37 (m, 2H), 4.28 (m, 2H), 4.17 (m, 4H), 4.07 (m, 2H), 3.85 (m, 2H), 2.53 (m, 4H), 1.88 (m, 4H), 1.30 (d, J=22.8 Hz, 6H), 1.23 (d, J=7.2 Hz, 6H).

Example 14

Preparation of a pharmaceutical composition in the form of a tablet. Starch (1600 mg), ground lactose (1600 mg), talc (400 mg), and (2R, 3R, 3aR, 11S, 13S, 15aR)-2-(2,4-dioxo-3,4-dihydro-2H-pyrimidin-cyclopentacyclotetradecene-5,10-dione (1(13)) (1000 mg) were mixed together and pressed into a bar. The resulting bar was comminuted into granules and sifted through a sieve to collect granules of 14-16 mesh. The granules thus obtained were shaped into tablets of a suitable form weighing 100-300 mg each.

Example 15

Preparation of a pharmaceutical composition in the form of capsules. (2R, 3R,3aR, 11S, 13S, 15aR)-2-(2,4-dioxo-3,4-dihydro-2H-pyrimidin-cyclopentacyclotetradecene-5,10-dione (1(13)) and lactose powder were carefully mixed in the ratio 2:1. The resultant powdery mixture was packed into gelatin capsules of a suitable size, 450 mg or 600 mg in each capsule.

Example 16

Preparation of a pharmaceutical composition in the form of capsules. (2R,3R,3aR,11S,13S,15aR)-2-(2,4-dioxo-3,4-dihydro-2H-pyrimidin-cyclopentacyclotetradecene-5,10-dione (1(13)) and AV-4047 or AV-4056, or AV-4058 and lactose powder were carefully mixed in the ratio 4:(0,5÷1):2. The resultant powdery mixture was packed into gelatin capsules of a suitable size, 350 mg or 700 mg in each capsule.

Example 17

Preparation of a pharmaceutical composition in the form of capsules. (2R, 3R, 3aR, 11S, 13S, 15aR)-2-(2,4-dioxo-3,4-dihydro-2H-pyrimidin-cyclopentacyclotetradecene-5,10-dione (1(13)), Daclatasvir (Daklinza, BMS790052) and lactose powder were carefully mixed in the ratio 4:1:2. The resultant powdery mixture was packed into gelatin capsules of a suitable size, 700 mg in each capsule.

Example 18

Anti-HCV activity (EC$_{50}$) and cytotoxicity (CC$_{50}$) of prodrugs of general formula 1. The HCV replicon assay was used to determine the antiviral activity of chemotherapeutic agents of general formula 1 (test compounds). Sovaldi (PSI-7977) was used as the reference drug. The test cell line used in the HCV Replicon Assay was the human hepatoma cell line Huh7 incorporating the HCV replicons synthesized by an outside vendor. 96-well plates were seeded with cells at a density of 7.5×10$^3$ cells per well in 50 µl of assay media. The compound stock solution was made up freshly in an assay medium (DMEM 1×, Cellgro; cat. #10-013-CV) as a 2× stock. A total of 11 serial 3-fold dilutions of test compounds were prepared from the 2× stock in the assay media ranging from 20 nM-0.2 pM final concentrations. At least 4 hours after seeding the cells, compound treatment was initiated by adding 50 µl of compound dilution to the plates. The final concentrations of compound therefore ranged from 10 nM to 0.1 pM when diluted 1:1 in culture media. The final DMSO concentration was 0.5%. Cells and inhibitors were incubated for 3 days at 37° C./5% CO$_2$. The media was removed from the plates by gentle tapping. The cells were fixed with 100 µl 1:1 acetone: methanol for 1 minute, washed three times with PBS buffer, and then blocked with 150 µl/well 10% Fetal Bovine Serum (FBS) in PBS for 1 hour at room temperature. The cells were then washed three times with PBS buffer and incubated with 100 µl/well anti-hepatitis C core mAb (Affinity BioReagents; cat. #MA1-080, 1 mg/ml stock diluted 1:4,000 in 10% FBS-PBS) for 2 hours at 37° C. Then, the cells were washed three times with PBS and incubated with 100 µl/well HRP-Goat Anti-Mouse antibody (diluted 1:3.500 in 10% FBS-PBS) for 1 hour at 37° C. The cells were then washed three times with PBS and developed with an OPD solution, 100 µl/well (1 OPD tablet+12 ml citrate/phosphate buffer+5 µl 30% H$_2$O$_2$ per plate), for 30 minutes in the dark at room temperature. The reaction was stopped with 2N H$_2$SO$_4$ (100 µl/well), and the absorbance was measured at A$_{490}$ X on a Victor$^3$ V 1420 Multilabel counter (Perkin Elmer). The EC$_{50}$ values were calculated for test compounds from the resulting best-fit equations determined by Xlfit software.

The cytotoxicity of the test compounds was studied in parallel using the same cell line, Huh7. Cell viability was determined using the ATPLite Kit (Perkin-Elmer, Boston, USA), according to manufacturer's instructions. 96-well black/transparent bottom plates were seeded with cells at a density of 7.5×10$^3$ cells per well in 50 µl medium. After 18 hours, compound treatment was initiated by adding 50 µl of compound dilution into the plates. Each compound dilution was tested in triplicates. The cells and inhibitors were then incubated for 96 hours at 37° C./5% CO$_2$. The plates were washed twice with PBS (0.2 ml/well), and then lysed by adding lysis buffer, 0.05 ml/well (all reagents were included with the ATPLite Kit). After rocking for 5 min on a rocking platform, substrate buffer was added (0.05 ml/well). After additional 5-min incubation, the plates were kept in dark for 10 min, and the luminescence was read using TopCount NXT (Packard, Perkin Elmer). CC$_{50}$ values for all test compounds were determined using XLfit 4.1 software.

Example 19

The human liver S9 fraction metabolic stability in human liver microsomal fraction of Macroheterocyclic nucleoside derivative represented by formula 1 and 2 and Sovaldi. Stock solutions of test compounds and PSI-352707 (10 mM) were prepared in DMSO and stored at −20° C. 10-× standard solutions of PSI-352707 (10, 8, 5, 2 and 1 µM) were prepared by dilution stock solution with water-acetonitrile mixture (1/1, v/v). The reaction mixture was prepared in a total volume of 350.5 µL containing 0.1 M potassium phosphate buffer (pH 7.4), 1 mM NADPH, 7 mM G6P, 1.5 U/mL G6PDH, 3.3 mM MgCl$_2$, 5 mM UDPGA, 122

μL deionised water and 1 μM test compound. The reaction mixture was pre-incubated at 400 rpm, 37° C. The reaction was initiated by adding 1 mg/mL human liver S9 fraction to the reaction mixture and incubated at 400 rpm, 37° C. At the desired times (0, 0.25, 0.5, 1, 2, 4, 6 8, 24 h), 30 μL aliquots were taken and the reaction was stopped by adding 180 μL acetonitrile containing 200 ng/ml of internal standard (IS, tolbutamide). Precipitation was performed on ice in refrigerator at +4° C. for 15 min. Then samples were centrifuged for 10 min at 3000 rpm. 150 μl of the supernatant were taken for LC-MS/MS analysis. To prepare PSI-352707 calibration samples 148 μL of supernatant after incubation without test compound were mixed with 2.1 μL of corresponding 10×-standard solution of PSI-352707.

LC-MS/MS analysis was performed on QTrap 5500 System (AB Sciex) combined with 1290 UPLC System (Agilent). Separation was achieved on BioBasic AX column (50×2.1 mm, 5μ, Thermo Scientific). Mobile phase consisted of solvent A (10 mm ammonium formate in water-acetonitrile mixture (7/3, v/v), pH 5.6), and solvent B (1 mM ammonium formate in water-acetonitrile mixture (7/3, v/v), pH 9.8). Elution was performed using step gradient (0-0.4 min 80% B. 0.8-2.0 min 40% B, 2.2-3.0 mm 80% B).

ABSciex QTrap 5500 Source (TurboIonSpray) was operated in negative ionization mode (Source temperature 650° C., Source gas 1 and Source gas 2-65 and 40 psi respectively). PSI-352707 and IS (tolbutamide) were detected in MRM mode by transitions with m/z 410 to 150 for H027-4261 (collision energy −30 kV) and 269/170 for tolbutamide (collision energy −25 kV). Flow rate was 0.5 mL/min, injection volume 1 μL. Data analysis and quantitation was performed in Analyst 1.5.2 Software (AB Sciex).

The invention claimed is:

1. Macroheterocyclic nucleoside derivative and its analogue of the general formula 1 or general formula 2, a stereoisomer, isotope-enriched analogue, pharmaceutically acceptable salt, hydrate and solvate thereof,

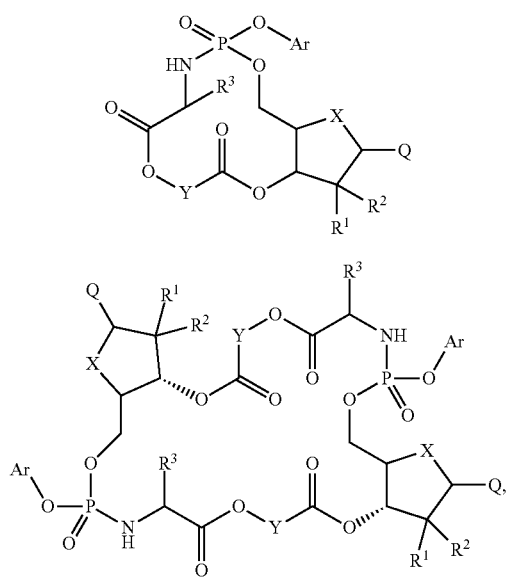

wherein:
Ar is aryl or hetaryl;
$R^1$ and $R^2$ are not necessarily the same substituents selected from H, F, Cl, $CH_3$ and OH;
$R^3$ is H or $CH_3$;
X is oxygen or ethanediyl-1,1 (C=$CH_2$);
Y is $CH(R^4)(CH_2)_k$ or $CH(R^4)(CH_2)_mC(O)O(CH_2)_n$;
$R^4$ is H or $CH_3$;
k has a value from zero to six;
m has a value from zero to two;
n has a value of one to four;
Q is a radical selected from Q1-Q4;

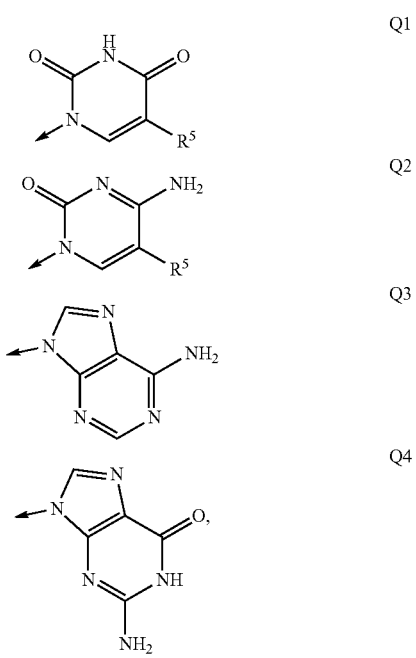

wherein: $R^5$ is the substituent selected from H, F, Cl, $CH_3$ and OH;
the arrow (→) indicates the location, joined by Q1-Q4.

2. The macroheterocyclic nucleoside derivative and its analogue according to claim 1 selected from the group consisting of: (2R,3aS,6S,9S,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(1/2)), (2R,3aS,6S,9S,11S,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(1)), (2R,3aS,6S,9S,11R,13aR)-2-(2,4-dioxo-3,4-dihydro-2H-pyrimidin-1-yl)-6,9-dimethyl-11-oxo-11-phenoxy-hexahydro-1,4,7,12-tetraoxa-10-aza-11-phospha-cyclopentacyclododecene-5,8-dione (1(2)), (2R,3R,3aR,6S,9S,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(3/4)), (2R,3R,3aR,6S,9S,11S,13aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(3)), (2R,3R,3 aR,6S,9S,11R,13 aR)-2-(2,4-dioxo-3,4-dihydro-2H-pyrimidin-1-yl)-3-fluoro-3,6,9-trimethyl-11-oxo-11-phenoxy-hexahydro-1,4,7,12-tetraoxa-10-aza-11-phospha-cyclopentacyclododecene-5,8-dione (1(4)), (2R,3R,3aR,10S, 14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(5/6)), (2R,3R,3aR,10S,12S,14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(5)), (2R,3R,3aR,10S,12R,14aR)-2-(2,4-dioxo-3,4-dihydro-2H-pyrimidin-1-yl)-3-fluoro-3,10-dimethyl-12-oxo-12-phenoxy-octahydro-1,4,8,13-tetraoxa-11-aza-12-phospha-cyclopentacyclotridecene-5,9-dione (1(6)), (2S,3aS,11S,15aR)-2-(2-amino-6-oxo-1,6-dihydro-purin-9-yl)-11-methyl-1-methylene-13-oxo-13-phenoxy-decahydro-4,9,14-trioxa-12-aza-13-phospha-cyclopentacyclotetradecene-5,10-dione (1(7/8)), (2S,3aS,11S,13S,15aR)-2-(2-amino-6-oxo-1,6-dihydro-purin-9-yl)-11-methyl-1-methylene-13-oxo-13-phenoxy-decahydro-4,9,14-trioxa-12-aza-13-phospha-cyclopentacyclotetradecene-5,10-dione (1(7)), (2S,3S,3aS,11S,13R,15aR)-2-(6-amino-purin-9-yl)-3,11-dimethyl-1-methylene-13-oxo-13-phenoxy-decahydro-4,9,14-trioxa-12-aza-13-phospha-cyclopentacyclotetradecene-5,10-dione (1(8)), (2R,3aS,11S,15aR)-2-(2,4-dioxo-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(9/10)), (2R,3aS,11S,13S,15aR)-2-(2,4-dioxo-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(9)), (2S,3aS,11S,13R,15aS)-11-methyl-2-(5-methyl-2,4-dioxo-3,4-dihydro-2H-pyrimidin-1-yl)-13-oxo-13-phenoxy-octahydro-1,4,9,14-tetraoxa-12-aza-13-phospha-cyclopentacyclotetradecene-5,10-dione (1(10)), (2R,3aS,11S,15aR)-2-(2,4-dioxo-5-trifluoromethyl-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(11/12)), (2R,3aS,11 S,13 S,15aR)-2-(2,4-dioxo-5-trifluoromethyl-3,4-dihydro-2H-pyrimidin-1-yl)-11-methyl-13-oxo-13-phenoxy-octahydro-1,4,9,14-tetraoxa-12-aza-13-phospha-cyclopentacyclotetradecene-5,10-dione (1(11)), (2S,3R,3aS,11S,13R,15aS)-3-fluoro-11-methyl-2-(5-methyl-2,4-dioxo-3,4-dihydro-2H-pyrimidin-1-yl)-13-oxo-13-phenoxy-octahydro-1,4,9,14-tetraoxa-12-aza-13-phospha-cyclopentacyclotetradecene-5,10-dione (1(12)), (2R,3R,3aR,11S,5aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(13/14)), 2R,3R,3aR,11 S,13 S,15aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(13)), (2R,3R,3aR,11 S,13R,15aR)-2-(2,4-dioxo-3,4-dihydro-2H-pyrimidin-1-yl)-3-fluoro-3,11-dimethyl-13-oxo-13-phenoxy-octahydro-1,4,9,14-tetraoxa-12-aza-13-phospha-cyclopentacyclotetradecene-5,10-dione (1(14)), (2R,3aR,11S,15aR)-2-(4-amino-2-oxo-2H-pyrimidin-1-yl)-3,3-difluoro-11-methyl-13-oxo-13-phenoxy-octahydro-1,4,9,14-tetraoxa-12-aza-13-phospha-cyclopentacyclotetradecene-5,10-dione (1(15/16)), (2R,3 aR,11S,13 S,15aR)-2-(4-amino-2-oxo-2H-pyrimidin-1-yl)-3,3-difluoro-11-methyl-13-oxo-13-phenoxy-octahydro-1,4,9,14-tetraoxa-12-aza-13-phospha-cyclopentacyclotetradecene-5,10-dione (1(15)), (2R,3aR,11 S,13R,15aR)-2-(4-amino-2-oxo-2H-pyrimidin-1-yl)-3,3-difluoro-11-methyl-13-oxo-13-phenoxy-octahydro-1,4,9,14-tetraoxa-12-aza-13-phospha-cyclopentacyclotetradecene-5,10-dione (1(16)), (2R,3R,3aR,12S,16aR)-2-(2,4-dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(17/18)), (2R,3R,3aR,12S,14S,16aR)-2-(2,4-dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(17)), (2R,3R,3aR,12S,14R,16aR)-2-(2,4-dioxo-3,4-dihydro-2H-pyrimidin-1-yl)-3-fluoro-3,12-dimethyl-14-oxo-14-phenoxy-decahydro-1,4,10,15-tetraoxa-13-aza-14-phospha-cyclopentacyclopentadecene-5,11-dione (1(18)), (2R,3R,3aR,13S,15S,17aR)-2-(2,4-dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(19/20)), (2R,3R,3aR,13S,15S,17aR)-2-(2,4-dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(19)), (2R,3R,3aR,13S,15R,17aR)-2-(2,4-dioxo-3,4-dihydro-2H-pyrimidin-1-yl)-3-fluoro-3,13-dimethyl-15-oxo-15-phenoxy-decahydro-1,4,11,16-tetraoxa-14-aza-15-phospha-cyclopentacyclohexadecene-5,12-dione (1(20)), (2R,3R,3aR,14S,16S,18aR)-2-(2,4-dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cycloheptadecene-5,13-dione (1(21/22)), (2R,3R,3aR,14S,16S,18aR)-2-(2,4-dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cyclopentacycloheptadecene-5,13-dione (1(21)), (2R,3R,3aR,14S,16R,18aR)-2-(2,4-dioxo-3,4-dihydro-2H-pyrimidin-1-yl)-3-fluoro-3,14-dimethyl-16-oxo-16-phenoxy-dodecahydro-1,4,12,17-tetraoxa-15-aza-16-phospha-cyclopentacycloheptadecene-5,13-dione (1(22)), (2R,3R,3aR,15S,17S,19aR)-2-(2,4-dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(23/24)), (2R,3R,3aR,15S,17S,19aR)-2-(2,4-dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(23)), (2R,3R,3aR,15S,17R,19aR)-2-(2,4-dioxo-3,4-dihydro-2H-pyrimidin-1-yl)-3-fluoro-3,15-dimethyl-17-oxo-17-phenoxy-dodecahydro-1,4,13,18-tetraoxa-16-aza-17-phospha-cyclopentacyclooctadecene-5,14-dione (1(24)), (2R,3R,3aR,12S,15S,17S,19aR)-2-(2,4-dioxo-3,4-dihydro-2H-pyrimidin-1-yl)-3-fluoro-3,12,15-trimethyl-17-oxo-17-phenoxy-decahydro-1,4,9,13,18-pentaoxa-16-aza-17-phospha-cyclopentacyclooctadecene-5,10,14-trione (1(25/26)), (2R,3R,3aR,12S,15S,17S,19aR)-2-(2,4-dioxo-3,4-dihydro-2H-pyrimidin-1-yl)-3-fluoro-3,12,15-trimethyl-17-oxo-17-phenoxy-decahydro-1,4,9,13,18-pentaoxa-16-aza-17-phospha-cyclopentacyclooctadecene-5,10,14-trione (1(25)), (2R,3R,3aR,15S,17R,19aR)-2-(2,4-dioxo-3,4-dihydro-2H-pyrimidin-1-yl)-3-fluoro-3,15-dimethyl-17-oxo-17-phenoxy-decahydro-1,4,8,13,18-pentaoxa-16-aza-17-phospha-cyclopentacyclooctadecene-5,9,14-trione (1(26)), (2R,3R,3aR,9S,11S,13aR,15R,16R,16aR,22S,24S,26aR)-2,15-bis(2,4-dioxo-3,4-dihydropyrimidin-1(2H)-yl)-3,16-difluoro-3,9,16,22-tetramethyl-11,24-diphenoxydodecahydro-2H,13H-difuro [3,2-j:3',2'-v][1,6,9,13,18,21,3,15,2,14] hexaoxadiazadiphosphacyclotetracosine-5,8,18,21 (6H,9H,19H,22H)-tetrone 11,24-dioxide (1(27)) and (2R,3R,3aR,11S,13S,15aR,17R,18R,18aR,26S,28S,30aR)-2,17-bis(2,4-dioxo-3,4-dihydropyrimidin-1(2H)-yl)-3,18-difluoro-3,11,18,26-tetramethyl-13,28-diphenoxyhexadecahydro-2H,15H-difuro[3,2-1:3',2'-z][1,6,11,15,20,25,3,17,2,16] hexaoxadiazadiphosphacyclooctacosine-5,10,20,25(6H, 11H,21H,26H)-tetrone 13,28-dioxide (1(28)), or a stereoisomer, isotope-enriched analogue, pharmaceutically acceptable salt, hydrate and solvate thereof.

3. A pharmaceutical composition comprising the compound according to claim 1 or 2 and a pharmaceutically acceptable medium.

4. A process for preparing the compounds according to claim 1 by cyclization of acid of general formula 3 or 16 and if necessary division of the latter on the stereoisomers

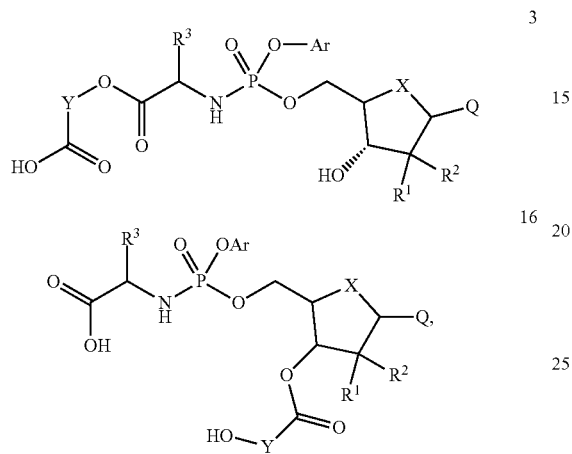

wherein: Ar, R$^1$, R$^2$, R$^3$, X, Y, and Q are as defined above.

* * * * *